(12) United States Patent
Samec et al.

(10) Patent No.: US 9,422,215 B2
(45) Date of Patent: Aug. 23, 2016

(54) CATALYTIC REDUCTIVE CLEAVAGE OF A β-O-4 BOND OF ETHERS OR POLYETHERS SUCH AS LIGNIN

(71) Applicant: KAT2BIZ AB, Stockholm (SE)

(72) Inventors: Joseph Samec, Spanga (SE); Maxim Galkin, Uppsala (SE); Joakim Löfstedt, Uppsala (SE)

(73) Assignee: KAT2BIZ AB, Stockholm (SE)

( * ) Notice: Subject to any disclaimer, the term of this patent is extended or adjusted under 35 U.S.C. 154(b) by 0 days.

(21) Appl. No.: 14/426,267

(22) PCT Filed: Sep. 9, 2013

(86) PCT No.: PCT/SE2013/051045
§ 371 (c)(1),
(2) Date: Mar. 5, 2015

(87) PCT Pub. No.: WO2014/039002
PCT Pub. Date: Mar. 13, 2014

(65) Prior Publication Data
US 2015/0218073 A1 Aug. 6, 2015

(30) Foreign Application Priority Data

Sep. 7, 2012 (WO) ................. PCT/SE2012/050948

(51) Int. Cl.
*C07C 45/29* (2006.01)
*C07C 29/48* (2006.01)
*C07G 1/00* (2011.01)
*C07C 51/235* (2006.01)

(52) U.S. Cl.
CPC ............... *C07C 45/29* (2013.01); *C07C 29/48* (2013.01); *C07C 51/235* (2013.01); *C07G 1/00* (2013.01)

(58) Field of Classification Search
CPC ...... C07C 45/29; C07C 45/48; C07C 51/235; C01G 1/00
See application file for complete search history.

(56) References Cited

U.S. PATENT DOCUMENTS

2013/0060071 A1 3/2013 Delledonne et al.

FOREIGN PATENT DOCUMENTS

| WO | WO-2011003029 A2 | 1/2011 |
| WO | WO-2011117705 A2 | 9/2011 |

OTHER PUBLICATIONS

Wu et al. Dalton Transactions, 2012, V.41, p. 11093-11106. (Disclosed in IDS).*
Wu, Adam et al. "Hydrogenolysis of β-O-4 lignin model dimers by a ruthenium-xantphos catalyst." *Dalton Transactions* 41 (2012): 11093-11106.
Wang, Xingyu and Roberto Rinaldi. "Solvent Effects on the Hydrogenolysis of Diphenyl Ether with Raney Nickel and their Implications for the Conversion of Lignin." *ChemSusChem* 5 (2012): 1455-1466.
Wang, Xingyu and Roberto Rinaldi. "Exploiting H-transfer reactions with Raney® Ni for upgrade of phenolic and aromatic biorefinery feeds under unusual, low-severity conditions." *Energy & Environmental Science* 5 (2012): 8244-8260.
Nagy, Máté et al. "Catalytic hydrogenolysis of ethanol organosolv lignin." *Holzforschung* 63 (2009): 513-520.
Zakzeski, Joseph et al. "Catalytic Lignin Valorization Process for the Production of Aromatic Chemicals and Hydrogen." *ChemSusChem* 5 (2012): 1602-1609.
Thring, Ronald W. and Jimmy Breau. "Hydrocracking of solvolysis lignin in a batch reactor." *Fuel* 75.7 (1996): 795-800.
International Search Report for PCT/SE2013/051045, mailed Dec. 20, 2013; ISA/SE.
International Preliminary Report on Patentability for PCT/SE2013/051045, issued Aug. 19, 2014; ISA/SE.

* cited by examiner

*Primary Examiner* — Yong Chu
(74) *Attorney, Agent, or Firm* — Harness, Dickey & Pierce, P.L.C.

(57) ABSTRACT

The present invention relates to a method of cleaving a β-O-4 bond to the corresponding C—H bond in a substrate, by use of a hydrogen donor and a metal catalyst in a solvent. Thereby it is possible to depolymerize a polymer having a repeating β-O-4 bond.

21 Claims, 27 Drawing Sheets
(2 of 27 Drawing Sheet(s) Filed in Color)

CATALYTIC REDUCTIVE CLEAVAGE OF A β-O-4 BOND OF ETHERS OR POLYETHERS SUCH AS LIGNIN

CROSS REFERENCE TO RELATED APPLICATIONS

This application is a U.S. National Phase Application under 35 U.S.C. 371 of International Application No. PCT/SE2013/051045 filed on Sep. 9, 2013 and published as WO 2014/039002 A1 on Mar. 13, 2014. This application is based on and claims priority from PCT/SE2012/050948 filed on Sep. 7, 2012. The entire disclosures of all of the above applications are incorporated herein by reference.

TECHNICAL FIELD

The present invention relates to a methodology to cleave the β-O-4 ether bond in a monomeric or polymeric compound.

BACKGROUND

Reductive cleavage of the β-O-4 bond in lignin is a rare transformation. One example using a simplified lignin model compound was performed by the Bergman group (Nichols, J. M.; Bishop, L. M.; Bergman, R. G.; Ellman, J. A. "Catalytic C—O Bond Cleavage of 2-Aryloxy-1-arylethanols and its Application to the Depolymerization of Lignin Related Polymers" *J. Am. Chem. Soc.* 2010, 132, 12554-12555). In this publication, a Ru-based catalyst performed the cleavage to generate the acetophenone and the phenol. A disadvantage is that inert atmosphere was required for efficient catalysis.

Very recently, a Ni catalyzed reduction of different model compounds and also pyrolysis oil was reported using isopropanol as hydrogen donor (X. Wang, R. Rinaldi, "Exploiting H-transfer reactions with RANEY Ni for upgrade of phenolic and aromatic biorefinery feeds under unusual, low-severity conditions", *Energy Environ. Sci.*, 2012, 5, 8244). The main transformation described in said publication is the reduction of the aromaticity in aromatic compounds to generate the saturated hydrocarbons. The authors also show with a few examples that phenolic and benzylic ethers are cleaved to generate saturated alcohols or hydrocarbons. However, the authors do not include the β-O-4 bond in a simplified or parent model. This bond is much more difficult to cleave than to cleave the highly activated phenolic and benzylic bonds, which are considered standard procedures. Another disadvantage with the previous report using Ni was that an excess of the metal was used. Thereby, the metal was not used in catalytic amount, and may only be considered to mediate and not catalyze the reaction.

It is well known that Ni is active in the hydrogenolysis of aryl ethers using hydrogen gas (A. G. Sergeev, J. F. Hartwig, "Selective, Nickel-catalyzed Hydrogenolysis of Aryl Ethers" *Science*, 2011, 332, 439-443). Also, that Ni and hydrogen gas or hydrogen donor is active in the reduction of the aromaticity in phenols and other aromatic compounds (C. Zhao, Y. Kou, A. A. Lemonidou, X. Li, J. A. Lercher, "Hydrodeoxygenation of bio-derived phenols to hydrocarbons using RANEY Ni and Nafion/SiO$_2$ catalysts," *Chem. Commun.*, 2010, 46, 412-414).

SUMMARY OF THE INVENTION

As described above, Ni with hydrogen or a hydrogen donor is known to reduce the aromaticity and also to cleave benzyl and phenyl ether bonds. However, the combination of Ni and a mild hydrogen donor is not known to cleave the β-O-4 bond in simplified or parent lignin model, lignin, lignosulfonate, or lignin from other pulping or separation method.

The object of the present invention is to provide a way to perform a cleavage of the β-O-4 bond in for example lignin using an alcohol as the hydrogen donor by means of catalysis. This has to the knowledge of the present inventors never before been presented.

The invention can be used in the depolymerization of lignin to generate hydrocarbon monomers that can be used as fine chemical feed-stock, fuel additives or as a component or starting material in fuel production.

One aspect of the present invention relates to a method of cleaving a β-O-4 bond to the corresponding C—H bond in a compound using a hydrogen donor and a transition metal based catalyst as defined in claim 1.

Another aspect of the present invention relates to a method in which the metal catalyst is not used in stoichiometric or over stoichiometric amount.

Preferred embodiments of the above mentioned aspect are described below; all the embodiments below should be understood to refer to both aspects described above.

In one embodiment the hydrogen donor is glycerol, glycol, glucose, isopropanol, methanol or ethanol.

In another embodiment one solvent is polar or non-polar and wherein said solvent may be protic or aprotic.

In another embodiment one solvent is selected between isopropanol, methanol, ethanol, water, ethylacetate, or a combination of two or more of the listed solvents.

In another embodiment the hydrogen donor is formic acid or hydrogen gas.

In another embodiment the hydrogen donor is not hydrogen gas.

In another embodiment the reaction is conducted at a temperature of at least 40° C., preferably 70-120° C.

In another embodiment the catalyst is nickel on carbon, Ni/Si, Ni/Fe, Nickel nanopowder or Raney nickel, or a palladium catalyst.

In another embodiment the compound is a β-O-4 bond in a lignin model compound.

In another embodiment the compound is a polymer.
In another embodiment the compound is a biopolymer.
In another embodiment the compound is lignin.
In another embodiment the compound is lignosulfonate.
In another embodiment the reaction is conducted in an atmosphere of carbon dioxide.

In another embodiment the catalyst is used in 0.1-500 mol %.

DESCRIPTION OF FIGURES

The patent or application file contains a drawing executed in color. Copies of this patent or patent application publication with a color drawing will be provided by the Office upon request and payment of the necessary fee.

DETAILED DESCRIPTION

Figure 1:
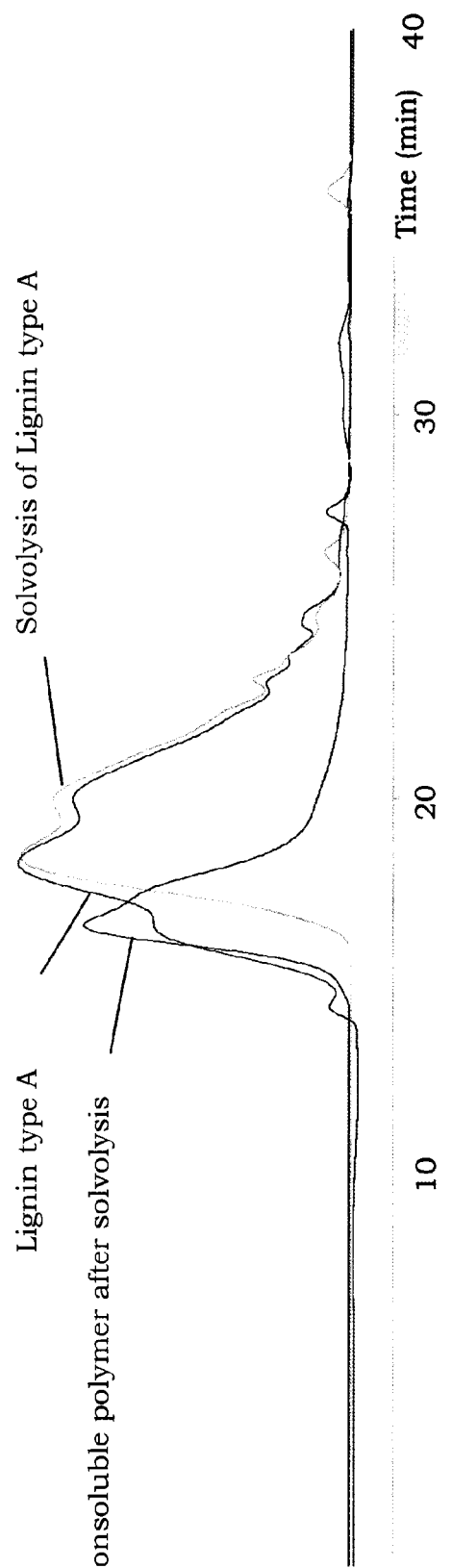
FIG. 1. GPC-results, Comparison of Lignin type A, solvolysis of Lignin type A and nonsoluble polymer after solvolysis.

In the present invention the term "hydrogen donor" should be interpreted as a substance or compound that gives or transfers hydrogen atoms to another substance or compound.

The invention relates to a method to cleave a substrate, wherein said substrate involves the β-O-4 bond,

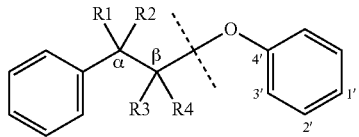

which is abundant in lignin. Without being bound by theory but it is believed that the cleavage is a reductive cleavage.

A general method comprises adding a catalyst to a reaction flask or container, adding a solvent followed by addition of a hydrogen donor and the substrate to be treated or cleaved. The reaction is then stopped or quenched and the obtained product is isolated and preferably dried. The method comprises of providing a set of components, a substrate to be cleaved, a hydrogen donor, a transition metal based catalyst and at least one solvent. The hydrogen donor is preferably an alcohol or a combination of alcohols. The components are then mixed to form a mixture. The mixing may be done using any suitable technique for example shaking or stirring. The order of addition of each component is not crucial. The mixture is heated to a temperature of not more than 200° C. and left to react, i.e. to cleave the β-O-4 bond in the substrate, for a suitable period of time.

The solvent may be a mixture of solvents or a second solvent may be added during the reaction wherein the second solvent may be reducing the aromatic parts of the substrate as well as cleaving β-O-4 bonds. In one embodiment the mixture contains iso-propanol. In another embodiment the second solvent is iso-propanol.

The method may further comprise one or more additional steps where the method is repeated. For example the method may comprise a first step as described above thereafter the obtained product (the cleaved substrate) may be isolated and dissolved in a second solvent together with a second catalyst. The second solvent may be the same as the solvent in the first step but may be a different solvent as well. For example the second solvent may be iso-propanol or a mixture comprising iso-propanol. The second catalyst may be the same as the catalyst in the first step. A base may added in the second step as well and the reaction mixture may be neutralized using any suitable acid. Before isolation the catalyst from the first step may be removed, for example by the use of a magnet. The isolation may be performed using any suitable technique and the isolated product may be washed with a suitable solvent for example water. The additional, or the second, step may be performed at a temperature of not higher than 200° C. The additional/second step is believed to reduce the aromatic feature (CH-groups in the rings are reduced to $CH_2$-groups) of the substrate and making the substrate more oil like, besides cleaving β-O-4 bonds. This solves the problem of dissolving the substrate in oils or solvents suitable for the fuel preparation steps for example. All embodiments described herein apply to both the first and the second step.

The phenyl group may be substituted in ortho, meta or para position. The reaction is performed using a transition metal catalyst (for example catalysts based on Ni, Pd, Pt) to generate the hydrocarbon in good (45-65% yield) to excellent yields (65-100% yield) with only water as side product. A suitable catalytic amount of catalyst can be 0.1 to 500 mol %, such as 0.5 mol % or more, or 1 mol % or more, or 2 mol % or more, or 4 mol % or more, or 5 mol % or more, or 8 mol % or more, or 400 mol % or less, or 250 mol % or less, or 200 mol % or less, or 150 mol % or less, or 100 mol % or less, or 50 mol % or less, or 20 mol % or less, or 15 mol % or less or 12 mol % or less or 10 mol % or less. The amount in equivalents may be at least 0.5 equivalents, or at least 1 equivalent, or at least 1.5 equivalent, or at least 2 equivalents, or at least 3 equivalents, or at least 4 equivalents.

The hydrogen donor may be any suitable compound that may act as a hydrogen donor, for example alcohol and/or formic acid. A non-limiting list of suitable alcohols is methanol (MeOH), ethanol (EtOH), propanol, iso-propanol (i-PrOH), glycerol, glycol, butanol, t-butanol (i-BuOH) or combinations thereof. In one embodiment the solvent is the hydrogen donor.

The reaction may be performed in any suitable solvent, or solvents, and the solvent may for example be selected from water, alkanes, alcohols, esters or ethers such as hexane, heptane, methanol (MeOH), ethanol (EtOH), propanol, iso-propanol (i-PrOH), glycerol, glycol, butanol, t-butanol (i-BuOH), ethyl acetate, or tert-butyl methyl ether (TBME), acetone or mixtures thereof. Non-limiting examples of mixtures are methanol-iso-propanol, methanol-t-butanol, ethanol-iso-propanol and hexane-iso-propanol. The solvents may be used as received or they may be degassed prior to use. In one embodiment at least one of the solvents are water when formic acid is used as a hydrogen donor. When the method is performed using two or more steps, the solvent of the first step may be an alcohol preferably methanol or ethanol, and the solvent of the second step an alcohol preferably iso-propanol.

In one embodiment the method is performed in the presence of an added base. A non-limiting list of suitable bases is KOH, NaOH, NaBH$_4$, ammonium formate (NH$_4$COOH) or K$_2$CO$_3$. The amount of base may be not more than 500 weight %, or not more than 400 weight %, or not more than 300 weight %, or not more than 200 weight %, or not more than 100 weight %. In one embodiment the amount of base is 10 weight % or more, or 50 weight % or more. Hydrogen peroxide (H$_2$O$_2$) may also be added, preferably dissolved in water, to form radicals in order to break down lignin. In order to neutralize the reaction mixture an acid may be added, for example HCl.

The reactions can be performed under mild reaction conditions (25° C.-200° C.) by conventional heating or by heating in a microwave oven, but can also be performed at higher reaction temperatures. In one embodiment the temperature is 180° C. or less, or 150° C. or less, or 120° C. or less. In another embodiment the temperature is 45° C. or more, or 70° C. or more, or 80° C. or more.

When using a carbon dioxide atmosphere, the atmosphere may comprise other compounds such as oxygen and nitrogen. The atmosphere could be air comprising carbon dioxide or an inert atmosphere (such as argon or nitrogen gas) comprising carbon dioxide.

The following compounds are non-limiting examples of substrates that could be treated or cleaved by the method according to the invention: phenylmethanesulfonic acid, 3-(4-(2-(4-hydroxy-3-methoxyphenyl)-2-oxoethoxy)phenyl)acrylaldehyde, ethyl 3-(4-(2-(4-hydroxy-3-methoxyphenyl)-2-oxoethoxy)phenyl)acrylate, 2-phenoxy-1-phenylethanone and 1,4-bis(benzo[d][1,3]dioxol-5-yl)hexahydrofuro[3,4-c]furan, 1-(3,4-dimethoxyphenyl)-2-(2-methoxyphenoxy)propane-1,3-diol, lignin, black liquor from Kraft pulping, green liquor, red or brown liquor, lignosulfonate, extracted or separated lignin or lignin from ethanol production.

When the substrate is a solution or mixture containing lignin, for example black or green liquor, the substrate may be pretreated in any suitable way. For example the substrate may be acidified and precipitated, solvolysed or filtrated using any suitable technique such as ultra- or microfiltration and/or cross-flow filtration for example.

In one embodiment the substrate is a sample comprising lignin or lignin derivatives having an average molecular weight of 5000 g/mol or less, or 3000 g/mol or less, or 1500 g/mol or less.

The method may cleave more than 50% of the present β-O-4 bonds, or preferably more than 75%, or preferably more than 90% or preferably more than 95%, or more than 98%, or even more preferably near 100% analyzed using 2D NMR (HSQC) (Bruker Avance II equipped with a QCI-P cryoprobe, 600 Mhz, solvent DMSO-d6/pyridine-d5 4:1.) at 298K. This cleavage percentage may in one embodiment be obtained within 50 hours, or preferably within 36 hours, or even more preferably within 18 hours, or even more preferably within 12 hours, preferably within 6 hours, or preferably within 2 hours, or even more preferably within 1 hour.

EXAMPLES

In some of the examples below the following lignin types have been used
Lignin type A—acid precipitated lignin from black liquor
Lignin type B—filtrated black liquor
Lignin type C—extracted from pine using dioxane, and
Lignin type D—from sulfite liquor
Lignin type E—from ethanol production Example 1

Reaction of Trans-Ferulic Acid

Trans-Ferulic acid (39 mg, 2×10$^{-4}$ mol) and wet Raney Ni 4200 (12 mg, 2×10$^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 35 mg of a reaction mixture which is, according to analysis by HNMR, 4-hydroxy-3-methoxy benzenepropanoic acid. The double bond was saturated.

Example 2

Reaction of Vanillin

Vanillin (31 mg, 2×10$^{-4}$ mol) and wet Raney Ni 4200 (12 mg, 2×10$^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 25 mg of a reaction mixture which is, according to analysis by HNMR, 2-methoxy-4-methylphenol. The aldehyde was reduced to methyl.

Example 3

Reaction of 4-Methyl Catechol

4-Methyl catechol (25 mg, 2×10$^{-4}$ mol) and wet Raney Ni 4200 (12 mg, 2×10$^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 20 mg of a reaction mixture which is, according to analysis by HNMR, a complex mixture of mainly, 2-hydroxy-4-methyl-Cyclohexanone; 2-hydroxy-5-methyl-Cyclohexanone; 4-methyl-1,2-Cyclohexanediol. The aromatic ring was saturated.

Example 4

Reaction of 4-hydroxybenzaldehyde 4-hydroxybenzaldehyde (25 mg, 2×10$^{-4}$ mol) and wet Raney Ni 4200 (12 mg, 2×10$^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 20 mg of a reaction mixture which is, according to analysis by HNMR, is 4-methylphenol. The aldehyde was reduced to methyl.

Example 5

Reaction of Syringaldehyde

Syringaldehyde (25 mg, 2×10$^{-4}$ mol) and wet Raney Ni 4200 (12 mg, 2×10$^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 20 mg of a reaction mixture which is, according to analysis by HNMR, is 2,6-dimethoxy-4-methylphenol. The aldehyde was reduced to methyl.

Example 6

Reaction of Catechol

Catechol (22 mg, $2 \times 10^{-4}$ mol) and wet Raney Ni 4200 (12 mg, $2 \times 10^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 20 mg of a reaction mixture which is, according to analysis by HNMR, a complex mixture of mainly, cyclohexane-1,2-diol. The aromatic ring was saturated.

Example 7

Reaction of 3-Methoxy catechol

3-Methoxy catechol (29 mg, $2 \times 10^{-4}$ mol) and wet Raney Ni 4200 (12 mg, $2 \times 10^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 26 mg of a reaction mixture which is, according to analysis by HNMR, a complex mixture of mainly, 3-methoxy cyclohexane-1,2-diol. The aromatic ring was saturated.

Example 8

Reaction of Para-Coumaric Acid

Para-Coumaric acid (32 mg, $2 \times 10^{-4}$ mol) and wet Raney Ni 4200 (12 mg, $2 \times 10^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 30 mg of a reaction mixture which is, according to analysis by HNMR, 3-(4-hydroxyphenyl)propanoic acid. The double bond was saturated.

Example 9

Reaction of 4-Hydroxyacetophenone

4-Hydroxyacetophenone (27 mg, $2 \times 10^{-4}$ mol) and wet Raney Ni 4200 (12 mg, $2 \times 10^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 25 mg of a reaction mixture which is, according to analysis by HNMR, 4-ethylcyclohexan-1-ol. The ketone and the aromatic ring were reduced.

Example 10

Reaction of 2,6-Dimethoxyphenol 2,6-Dimethoxyphenol (30 mg, $2 \times 10^{-4}$ mol) and wet Raney Ni 4200 (12 mg, $2 \times 10^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 28 mg of a reaction mixture which is, according to analysis by HNMR, starting material+cyclohexanol. The aromatic ring was saturated.

Example 11

Reaction of Guaiacol

Guaiacol (24 mg, $2 \times 10^{-4}$ mol) and wet Raney Ni 4200 (12 mg, $2 \times 10^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 20 mg of a reaction mixture which is, according to analysis by HNMR, starting material+phenol+cyclohexanol. The aromatic ring was partly saturated.

Example 12

Reaction of Phenol

Phenol (18 mg, $2 \times 10^{-4}$ mol) and wet Raney Ni 4200 (12 mg, $2 \times 10^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 10 mg of a reaction mixture which is, according to analysis by HNMR, cyclohexanol. The aromatic ring was saturated.

Example 13

Reaction of 3,5-Dimethoxy-4-hydroxyacetophenone 3,5-Dimethoxy-4-hydroxyacetophenone (39 mg, $2 \times 10^{-4}$ mol) and wet Raney Ni 4200 (12 mg, $2 \times 10^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 35 mg of a reaction mixture which is, according to analysis by HNMR, 4-ethylphenol+4-ethylcyclohexan-1-ol. The ketone was reduced and the aromatic ring was partly reduced.

Example 14

Reaction of Acetovanillone

Acetovanillone (33 mg, $2 \times 10^{-4}$ mol) and wet Raney Ni 4200 (12 mg, $2 \times 10^{-4}$ mol, 100 mol %) is weighed into a reaction flask under argon. Degassed i-PrOH (5 mL) is added and the flask is capped with a rubber septa and the mixture is heated (80° C.). The reaction is run for 24 hours and the reaction mixture is cooled. Nickel was removed with a magnet. Concentration gave 30 mg of a reaction mixture which is, according to analysis by HNMR, only non-aromatic compounds 4-ethylcyclohexan-1-ol. The ketone/aromatic ring was reduced.

Example 15

Reaction of 2-phenoxy-1-phenylethan-1-ol 2-phenoxy-1-phenylethan-1-ol (30 mg, $1.4 \times 10^{-4}$ mol) and wet Raney Ni 4200 (25 mg, $4.2 \times 10^{-4}$ mol, 100 mol %) is weighed into a reaction flask under argon. Degassed i-PrOH (5 mL) is added and the flask is capped with a rubber septa and the mixture is heated (80° C.). The reaction is run for 18 hours and the reaction mixture is cooled. Nickel was removed with a magnet. Concentration gave 25 mg of a reaction mixture which is, according to analysis by HNMR, 1-cyclohexylethan-1-ol. The β-O-4 bond was broken and the aromatic ring was saturated.

Example 16

Reaction of 2-(2-methoxyphenoxy)-1-(4-methoxyphenyl)ethan-1-ol 2-(2-methoxyphenoxy)-1-(4-methoxyphenyl)ethan-1-ol (30 mg, $1.4 \times 10^{-4}$ mol) and wet Raney Ni 4200 (25 mg, $4.2 \times 10^{-4}$ mol, 100 mol %) is weighed into a reaction flask under argon. Degassed i-PrOH (5 mL) is added and the flask is capped with a rubber septa and the mixture is heated (80° C.). The reaction is run for 18 hours and the reaction mixture is cooled. Nickel was removed with a magnet. Concentration gave 25 mg of a reaction mixture which is, according to analysis by HNMR, is 1-(4-methoxyphenyl)ethan-1-ol and 2-methoxyphenol. The β-O-4 bond was 100% broken.

Example 17

Reaction of 2-(2-methoxyphenoxy)-1-(4-methoxyphenyl)ethan-1-ol

To a vial was added wet Raney Ni 4200 (8 mg, $7 \times 10^{-5}$ mol, 50 mol %) then 3 mL hexane followed by 2-(2-methoxyphenoxy)-1-(4-methoxyphenyl)ethan-1-ol (38 mg, $1.4 \times 10^{-4}$ mol) and of $NaBH_4$ (3 mg, $7 \times 10^{-5}$ mol, 50 mol %). The vial was capped and heated to 80° C. for 24 hours. The reaction was cooled, opened and 10 mg of $NH_4COOH$ was added. 50 mL of $Et_2O$ was used to transfer the crude to an erlenmeyer containing $MgSO_4$. After drying the solution was filtered and concentrated. HNMR gave 63% conversion to 1-(4-methoxyphenyl)ethan-1-one and 1-(4-methoxyphenyl)ethan-1-ol in a ratio 3:7. 63% of the β-O-4 bond was broken.

Example 18

Reaction of 2-(2-methoxyphenoxy)-1-(4-methoxyphenyl)ethan-1-ol

To a vial was added wet Raney Ni 4200 (8 mg, $7 \times 10^{-5}$ mol, 50 mol %), then 3 mL degassed hexane followed by 2-(2-methoxyphenoxy)-1-(4-methoxyphenyl)ethan-1-ol (38 mg, $1.4 \times 10^{-4}$ mol). The vial was capped and heated to 80° C. for 24 hours. The reaction was cooled, opened and 10 mg of $NH_4COOH$ was added. 50 mL of $Et_2O$ was used to transfer the crude to an erlenmeyer containing $MgSO_4$. After drying the solution was filtered and concentrated. HNMR gave 88% conversion to 1-(4-methoxyphenyl)ethan-1-one and only traces of 1-(4-methoxyphenyl)ethan-1-ol was detected. 88% of the β-O-4 bond was broken.

Example 19

Reaction of 2-(2-methoxyphenoxy)-1-(4-methoxyphenyl)ethan-1-ol

Wet Raney Ni 4200 was dried under vacuum and carefully weight (20 mg (dry weight), $3.5 \times 10^{-4}$ mol, 250 mol %). 4 mL degassed heptane was added, followed by 2-(2-methoxyphenoxy)-1-(4-methoxyphenyl)ethan-1-ol (38 mg, $1.4 \times 10^{-4}$ mol). The reaction was heated at 120° C. for 24 hours. Workup: The reaction was cooled, opened and 10 mg of $NH_4COOH$ was added. 50 mL of $Et_2O$ was used to transfer the crude to an erlenmeyer containing $MgSO_4$. After drying the solution was filtered and concentrated. HNMR gave 100% conversion to 1-(4-methoxyphenyl)ethan-1-one, 100% of the β-O-4 bond was broken.

Example 20

Reaction of 2-(2-methoxyphenoxy)-1-(4-methoxyphenyl)ethan-1-ol

Wet Raney Ni 4200 was dried under vacuum and carefully weight (39 mg (dry weight), $6.8 \times 10^{-4}$ mol, 150 mol %). 6 mL degassed heptane was added, followed by 2-(2-methoxyphenoxy)-1-(4-methoxyphenyl)ethan-1-ol (120 mg, $4.4 \times 10^{-4}$ mol). The reaction was heated at 120° C. for 24 hours. The reaction was cooled, opened and 10 mg of $NH_4COOH$ was added. 50 mL of $Et_2O$ was used to transfer the crude to an erlenmeyer containing $MgSO_4$. After drying the solution was filtered and concentrated. HNMR gave 38% conversion to 1-(4-methoxyphenyl)ethan-1-one, 38% of the β-O-4 bond was broken.

Example 21

Reaction of Reference Compounds 2-(2-methoxyphenoxy)-1-(4-methoxyphenyl)propane-1,3-diol (24 mg, $8 \times 10^{-5}$ mol) and wet Raney Ni 4200 (23 mg, $3.9 \times 10^{-4}$ mol, 500 mol %) and KOH (13 mg, $2.4 \times 10^{-4}$ mol, 300%) is weighed into a reaction flask under argon. Degassed MeOH (2 mL) is added and the flask is capped with a rubber septa and the mixture is heated (120° C.). The reaction is run for 24 hours and the reaction mixture is cooled. Nickel was removed with a magnet. Concentration gave 10 mg of a reaction mixture which is, according to analysis by HNMR, contains a complex mixture of starting material and decomposition products.

Example 22

Reaction of Reference Compounds 2-(2-methoxyphenoxy)-1-(4-methoxyphenyl)propane-1,3-diol (24 mg, $8 \times 10^{-5}$ mol) and wet Raney Ni 4200 (23 mg, $3.9 \times 10^{-4}$ mol, 500 mol %) is weighed into a reaction flask under argon. Degassed i-PrOH (2 mL) is added and the flask is capped with a rubber septa and the mixture is heated (120° C.). The reaction is run for 24 hours and the reaction mixture is cooled. Nickel was removed with a magnet. Concentration gave 10 mg of a reaction mixture which, according to analysis by HNMR, contains a complex mixture of nonaromatic decomposition products and no starting material.

Example 23

Reaction of Reference Compounds 2-(2-hydroxyphenyl)phenol (20 mg, $1.1\times10^{-4}$ mol) and wet Raney Ni 4200 (32 mg, $5.4\times10^{-4}$ mol, 500 mol %) is weighed into a reaction flask under argon. Degassed i-PrOH (2 mL) is added and the flask is capped with a rubber septa and the mixture is heated (120° C.). The reaction is run for 24 hours and the reaction mixture is cooled. Nickel was removed with a magnet. Concentration gave 10 mg of a reaction mixture which is, according to analysis by HNMR, contains 2-(2-hydroxycyclohexyl)cyclohexan-1-ol. The aromatic rings were saturated.

Example 24

Reaction of Reference Compounds

5-[4-(2H-1,3-benzodioxol-5-yl)-hexahydrofuro[3,4-c]furan-1-yl]-2H-1,3-benzodioxole (38 mg, $1.1\times10^{-4}$ mol) and wet Raney Ni 4200 (32 mg, $5.4\times10^{-4}$ mol, 500 mol %) is weighed into a reaction flask under argon. Degassed i-PrOH (2 mL) is added and the flask is capped with a rubber septa and the mixture is heated (120° C.). The reaction is run for 24 hours and the reaction mixture is cooled. Nickel was removed with a magnet. Concentration gave 20 mg of a reaction mixture which, according to analysis by HNMR, contains 4-[4-(3,4-dihydroxycyclohexyl)-hexahydrofuro[3,4-c]furan-1-yl]cyclohexane-1,2-diol. The aromatic rings were saturated.

Example 25

Reaction of Reference Compounds

Phenoxybenzene (18 mg, $1.1\times10^{-4}$ mol) and wet Raney Ni 4200 (32 mg, $5.4\times10^{-4}$ mol, 500 mol %) is weighed into a reaction flask under argon. Degassed i-PrOH (2 mL) is added and the flask is capped with a rubber septa and the mixture is heated (120° C.). The reaction is run for 4 hours and the reaction mixture is cooled. Nickel was removed with a magnet. Concentration gave 10 mg of a reaction mixture which is, according to analysis by HNMR, contains cyclohexanol. The aromatic rings were saturated and the ether bond was cleaved.

Example 26

Solvolysis of Lignin Type A

To 40 mg of Lignin type A under Argon, was added 4 mL degassed EtOH and the reaction was stirred at 120° C. for 50 hours. Solids were visible. The reaction was cooled and the solvent (without solids) was transferred to a clean round bottom flask. The solvent was evaporated to yield 20 mg of product which was dissolved in 1.3 mL of THF, filtered through a syringe-filter into a HPLC-vial. The remaining solid (7 mg) was dissolved in THF, filtered through a syringe-filter into a HPLC-vial. Both are injected into an HPLC-system (GPC).

See FIG. 1, Comparison of Lignin type A, solvolysis of Lignin type A and nonsoluble polymer after solvolysis.

Example 27

Reaction of Lignin Type A with Nickel Nanoparticles and Base

Nickel nanoparticles (4 mg, $7\times10^{-4}$ mol, 30 mol %) and Lignin type A (40 mg, $2.2\times10$-4 mol, 300 mol %), is weighed into a reaction flask under argon. Degassed ethanol (4 mL) is added and the flask is capped with a rubber septa and the mixture is heated (120° C.). The reaction is run for 50 hours and the reaction mixture is cooled. Nickel was removed with a magnet, and the reaction mixture is injected into an HPLC-system (GPC).

Figure 2:
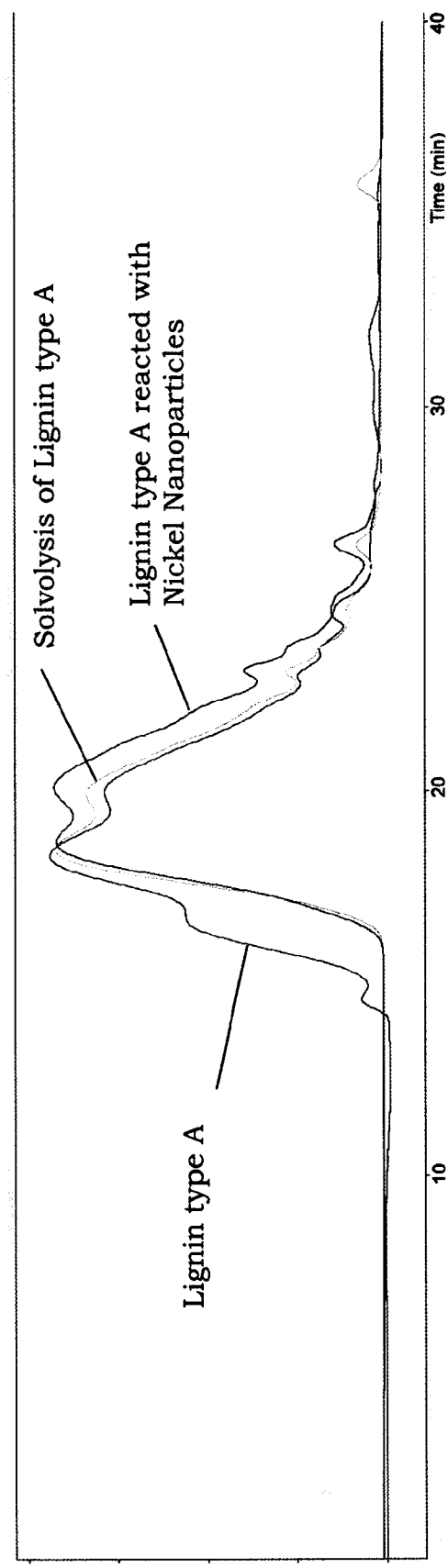
FIG. 2, GPC-results. Comparison of Lignin type A, solvolysis of Lignin type A, and Lignin type A reacted with Nickel Nanoparticles.

See FIG. 2, Comparison of Lignin type A, solvolysis of Lignin type A, and Lignin type A reacted with Nickel Nanoparticles.

Example 28

Reaction of Lignin Type A with Nickel Nanoparticles and Base

Nickel nanoparticles (4 mg, $7\times10^{-4}$ mol, 30 mol %), NaBH$_4$ (25 mg, $6.7\times10^{-4}$ mol, 300 mol %) and Lignin type A (40 mg, $2.2\times10^{-4}$ mol, dry), is weighed into a reaction flask under argon. Degassed ethanol (4 mL) is added and the flask is capped with a rubber septa and the mixture is heated (120° C.). The reaction is run for 50 hours and the reaction mixture is cooled. Nickel was removed with a magnet, and the reaction mixture is injected into an HPLC-system (GPC).

Example 29

Reaction of Lignin Type A with Nickel Nanoparticles and Base

Nickel nanoparticles (4 mg, $7\times10^{-4}$ mol, 30 mol %), KOH (37 mg, $6.7\times10^{-4}$ mol, 300 mol %) and Lignin type A (40 mg, $2.2\times10$-4 mol, dry), is weighed into a reaction flask under argon. Degassed ethanol (4 mL) is added and the flask is capped with a rubber septa and the mixture is heated (120° C.). The reaction is run for 50 hours and the reaction mixture is cooled. Nickel was removed with a magnet, and the reaction mixture is injected into an HPLC-system (GPC).

Example 30

Reaction of Lignin Type A with Nickel Nanoparticles and Base

Nickel nanoparticles (4 mg, $7\times10^{-4}$ mol, 30 mol %), K$_2$CO$_3$ (46 mg, $3.3\times10^{-4}$ mol, 150 mol %) and Lignin type A (40 mg, $2.2\times10^{-4}$ mol, dry), is weighed into a reaction flask under argon. Degassed ethanol (4 mL) is added and the flask is capped with a rubber septa and the mixture is heated (120° C.). The reaction is run for 50 hours and the reaction mixture is cooled. Nickel was removed with a magnet, and the reaction mixture is injected into an HPLC-system (GPC).

Figure 3:
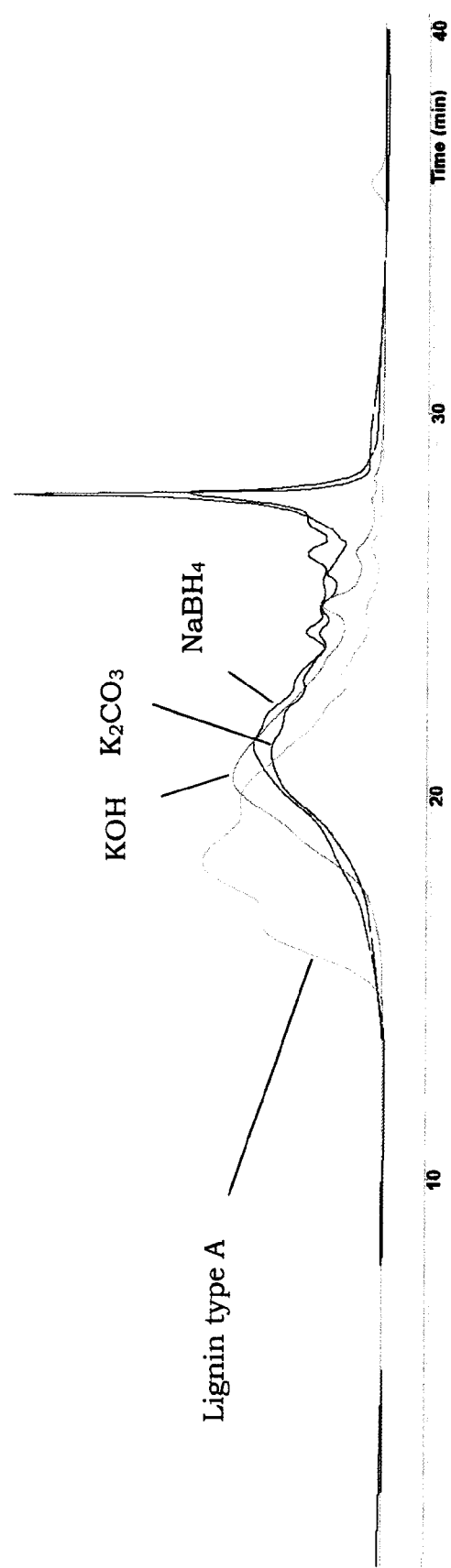
FIG. 3, GPC-results showing the results from the reaction mixtures, Lignin type A reacted with NaBH$_4$, KOH and K$_2$CO$_3$.

See FIG. 3, show the results from the reaction mixtures, Lignin type A reacted with NaBH$_4$, KOH and K$_2$CO$_3$.

Example 31

Reaction of Lignin Type A with Nickel Nanoparticles and Hydrogen Peroxide

Nickel nanoparticles (6 mg, $6\times10^{-5}$ mol, 15 mol %) and Lignin type A (40 mg, $2.2\times10^{-4}$ mol, dry), is weighed into a reaction flask under argon. Degassed ethanol (3 mL) is added followed by $H_2O_2$ (0.2 mL, 30% in water, $1.78 \times 10^{-3}$ mol, 800%). The flask is capped with a rubber septa and the mixture is heated (80° C.). The reaction is run for 18 hours and the reaction mixture is cooled. Nickel was removed with a magnet, and the mixture is neutralized. The reaction mixture is injected into an HPLC-system (GPC).

Example 32

Reaction of Lignin Type A with Nickel Nanoparticles and Hydrogen Peroxide

Nickel nanoparticles (16 mg, $2.7 \times 10^{-4}$ mol, 40 mol %) and Lignin type A (40 mg, $2.2 \times 10^{-4}$ mol, dry), is weighed into a reaction flask under argon. Degassed ethanol (3 mL) is added followed by of $H_2O_2$ (0.2 mL, 30% in water, $1.78 \times 10^{-3}$ mol, 800%). The flask is capped with a rubber septa and the mixture is heated (80° C.). The reaction is run for 18 hours and the reaction mixture is cooled. Nickel was removed with a magnet, and the mixture is neutralized. The reaction mixture is injected into an HPLC-system (GPC).

Example 33

Reaction of Lignin Type A with Nickel Nanoparticles and Hydrogen Peroxide

Nickel nanoparticles (43 mg, $7.3 \times 10^{-4}$ mol, 110 mol %) and Lignin type A (120 mg, $6.7 \times 10^{-4}$ mol, dry), is weighed into a reaction flask under argon. Degassed ethanol (3 mL) is added followed by $H_2O_2$ (0.3 mL, 30% in water, $2.67 \times 10^{-3}$ mol, 400%). The flask is capped with a rubber septa and the mixture is heated (80° C.). The reaction is run for 18 hours and the reaction mixture is cooled. Nickel was removed with a magnet, and the mixture is neutralized. The reaction mixture is injected into an HPLC-system (GPC).

Figure 4:
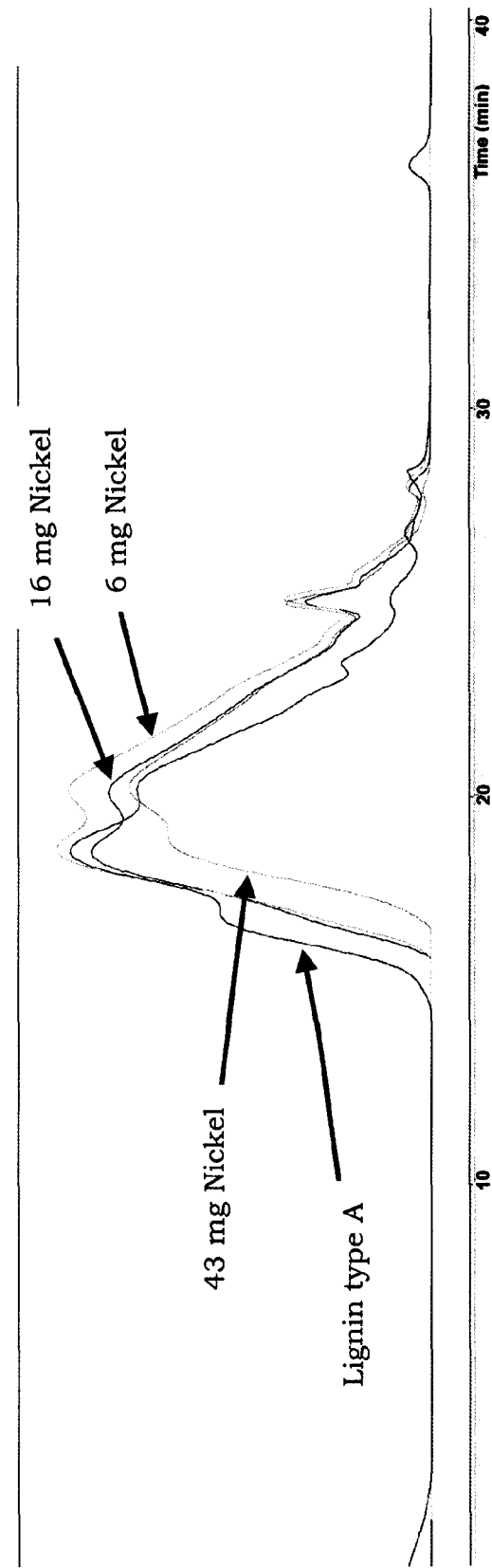
FIG. 4, GPC-results showing the results from the reaction mixtures Lignin type A reacted with 6 mg Nickel, 16 mg Nickel and 43 mg Nickel.

See FIG. 4, show the results from the reaction mixtures Lignin type A reacted with 6 mg Nickel, 16 mg Nickel and 43 mg Nickel.

Example 34

Reaction of Lignin Type A

Nickel nanoparticles (3 mg, $6 \times 10^{-4}$ mol, 25 mol %), KOH (37 mg, $6.7 \times 10^{-4}$ mol, 300%) and Lignin type A (40 mg, 2.2x10-4 mol, dry), is weighed into a reaction flask under argon. Degassed ethanol (3 mL) is added and the flask is capped with a rubber septa and the mixture is heated (120° C.). The reaction is run for 18 hours and the reaction mixture is cooled. Nickel was removed with a magnet, and the mixture is neutralized. The reaction mixture is injected into an HPLC-system (GPC).

Figure 5:
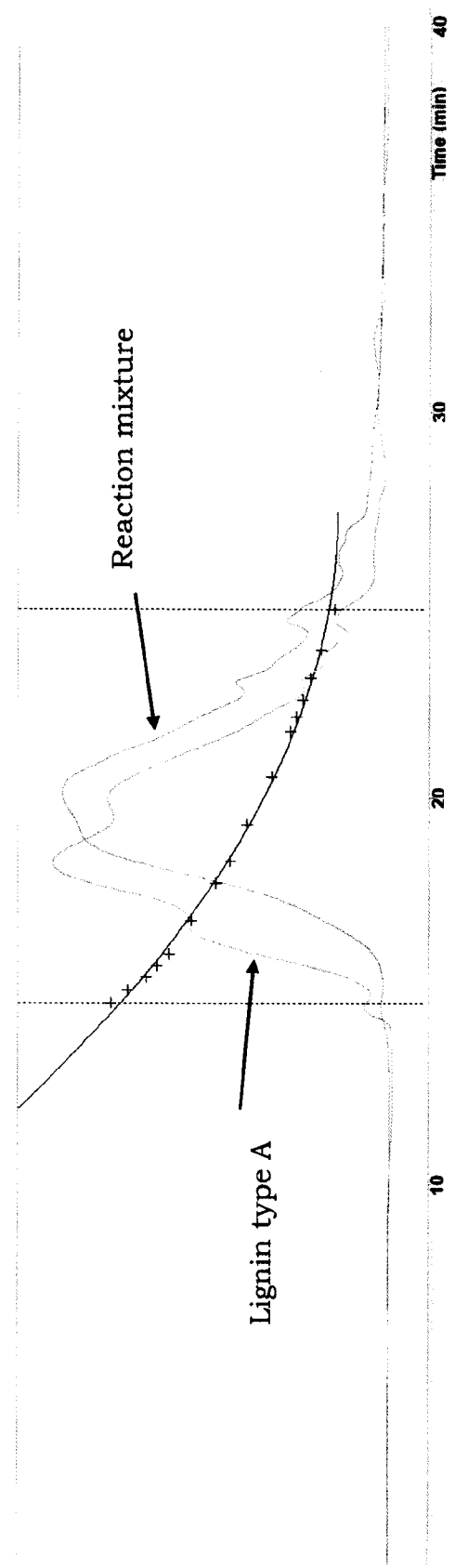
FIG. 5, shows the results from the reaction mixtures

See FIG. 5, show the results from the reaction mixture.

Example 35

Reaction of Lignin Type B

Wet Raney Ni 4200 (~70 mg, $1 \times 10^{-3}$ mol, 500 mol %), KOH (37 mg, $6.7 \times 10^{-4}$ mol, 300%) and Lignin type B (40 mg, $2.2 \times 10^{-4}$ mol, dry), is weighed into a reaction flask under argon. Degassed methanol (3 mL) is added and the flask is capped with a rubber septa and the mixture is heated (120° C.). The reaction is run for 18 hours and the reaction mixture is cooled. Nickel was removed with a magnet, and the mixture is neutralized. The reaction mixture is injected into an HPLC-system (GPC).

Figure 6:
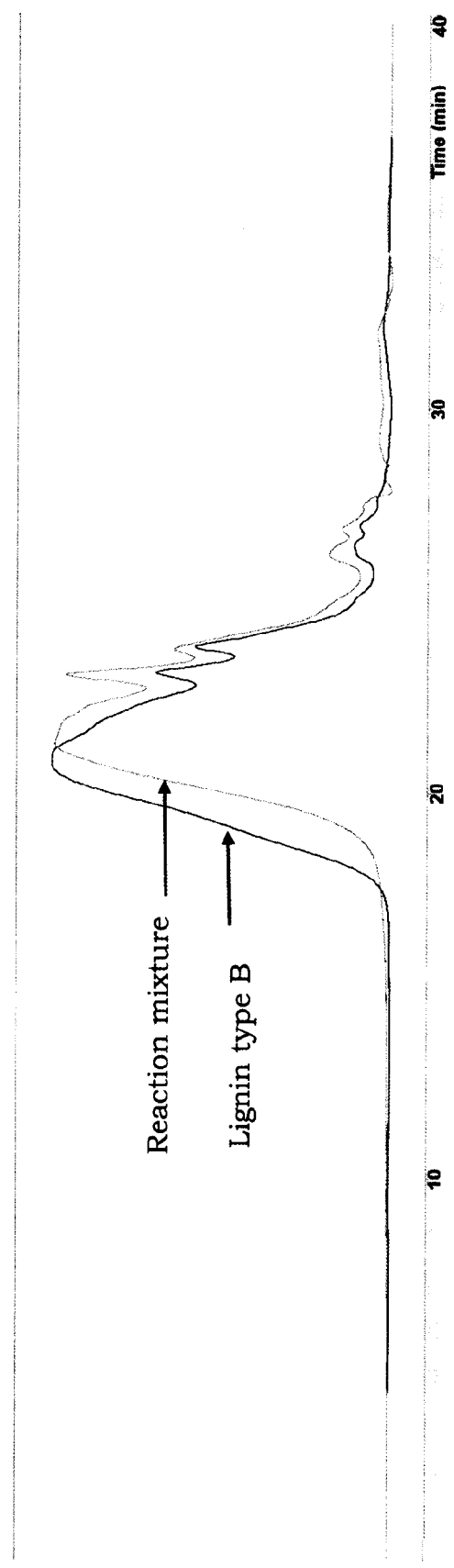
FIG. 6, shows the results from the reaction mixtures

See FIG. 6, show the results from the reaction mixtures

Example 36

Reaction of Lignin Type B

Nickel nanoparticles (15 mg, $2.4 \times 10^{-3}$ mol, 110 mol %) and Lignin type B (40 mg, $2.2 \times 10^{-4}$ mol, dry), is weighed into a reaction flask under argon. Degassed ethanol (3 mL) is added followed by $H_2O_2$ (0.2 mL, 30% in water, $1.78 \times 10^{-3}$ mol, 800%). The flask is capped with a rubber septa and the mixture is heated to 80° C. The reaction is run for 18 hours and the reaction mixture is cooled. Nickel was removed with a magnet, and the mixture is neutralized. The reaction mixture is injected into an HPLC-system (GPC).

Example 37

Reaction of Lignin Type B

Wet Raney Ni 4200 (~70 mg, $1 \times 10^{-3}$ mol, 500 mol %), KOH (37 mg, $6.7 \times 10^{-4}$, mol, 300%) and Lignin type B (40 mg, $2.2 \times 10^{-4}$ mol, dry), is weighed into a reaction flask under argon. Degassed ethanol (3 mL) is added followed by $H_2O_2$ (0.2 mL, 30% in water, $1.78 \times 10^{-3}$ mol, 800%). The flask is capped with a rubber septa and the mixture is heated to 80° C. The reaction is run for 18 hours and the reaction mixture is cooled. Nickel was removed with a magnet, and the mixture is neutralized. The reaction mixture is injected into an HPLC-system (GPC).

Figure 7:
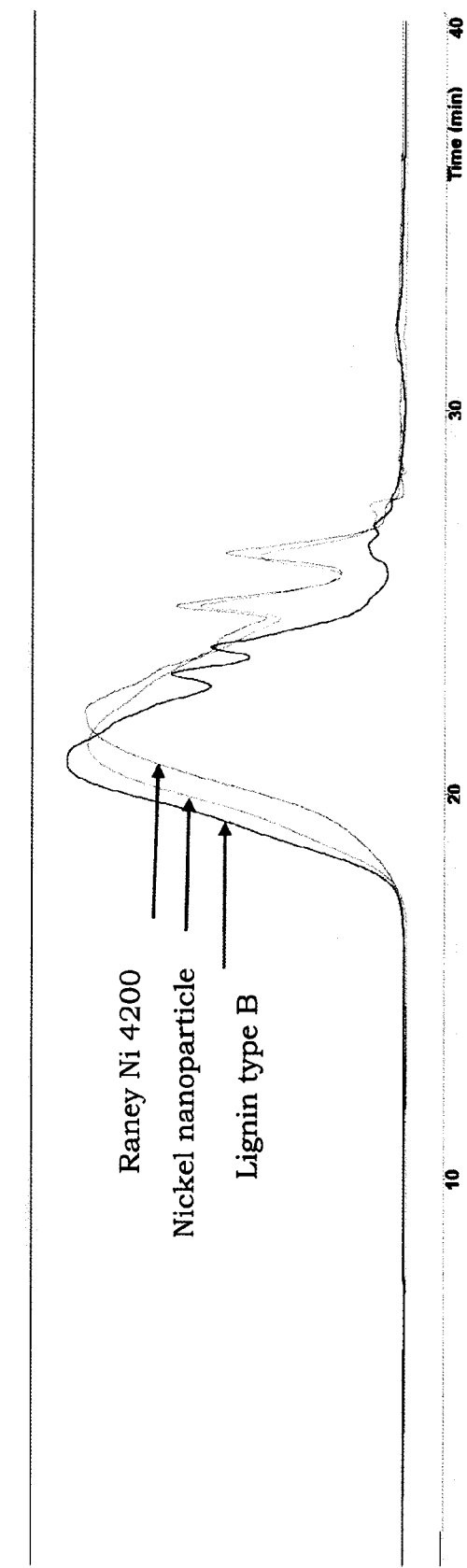
FIG. 7, shows the results from the reaction mixtures of Lignin type B with Nickel nanoparticle and Raney Nickel.

See FIG. 7, show the results from the reaction mixtures Reaction of Lignin type B with Nickel nanoparticle and Raney Nickel.

Example 38

Reaction of Lignin Type B

Wet Raney Ni 4200 (~70 mg, $1 \times 10^{-3}$ mol, 500 mol %), KOH (37 mg, $6.7 \times 10^{-4}$ mol, 300%) and Lignin type B (40 mg, $2.2 \times 10^{-4}$ mol, dry), is weighed into a reaction flask under argon. Degassed methanol (3 mL) is added and the flask is capped with a rubber septa and the mixture is heated (120° C.). The reaction is run for 18 hours and the reaction mixture is cooled. Nickel was removed with a magnet, and the mixture is neutralized. The reaction mixture is injected into an HPLC-system (GPC) and analyzed by 2dNMR (HSQC). The size was reduced and no β-O-4 bonds could be detected.

Example 39

Reaction of Lignin Type B, t-BuOH Effect

Wet Raney Ni 4200 (~70 mg, $1 \times 10^{-3}$ mol, 500 mol %), KOH (37 mg, $6.7 \times 10^{-4}$ mol, 300%) and Lignin type B (40 mg, $2.2 \times 10^{-4}$ mol, dry), is weighed into a reaction flask under argon. Degassed methanol/t-BuOH 1:1 (3 mL) is added and the flask is capped with a rubber septa and the mixture is heated (120° C.). The reaction is run for 18 hours and the reaction mixture is cooled. Nickel was removed with a magnet, and the mixture is neutralized. The reaction mixture is injected into an HPLC-system (GPC).

Example 40

Reaction of Lignin Type B, t-BuOH Effect

Wet Raney Ni 4200 (~70 mg, $1\times10^{-3}$ mol, 500 mol %), KOH (37 mg, $6.7\times10^{-4}$ mol, 300%) and Lignin type B (40 mg, $2.2\times10^{-4}$ mol, dry), is weighed into a reaction flask under argon. Degassed t-BuOH (3 mL) is added and the flask is capped with a rubber septa and the mixture is heated (120° C.). The reaction is run for 18 hours and the reaction mixture is cooled. Nickel was removed with a magnet, and the mixture is neutralized. The reaction mixture is injected into an HPLC-system (GPC).

Figure 8:
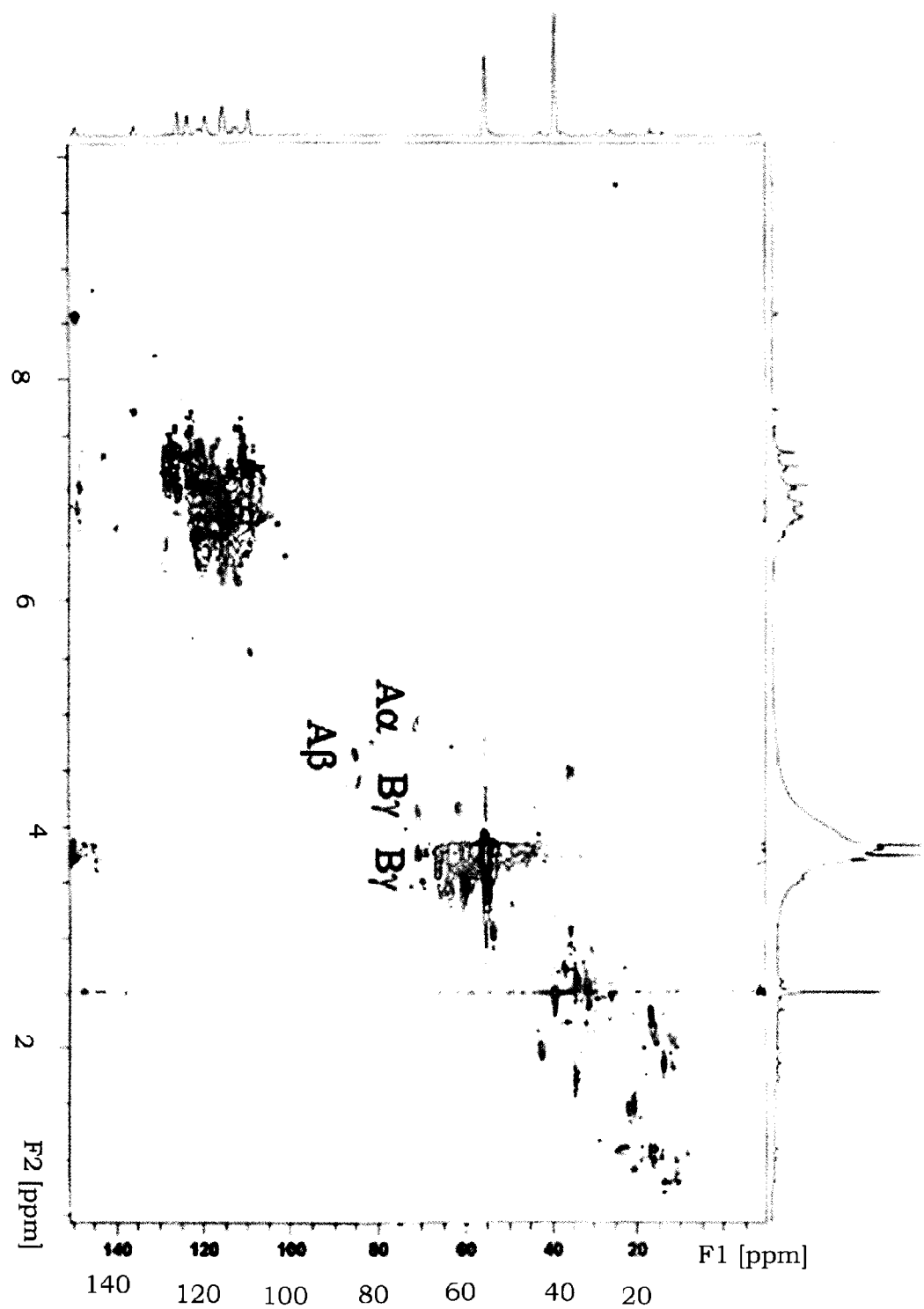
FIG. 8, HSQC of Lignin type B
Figure 9:
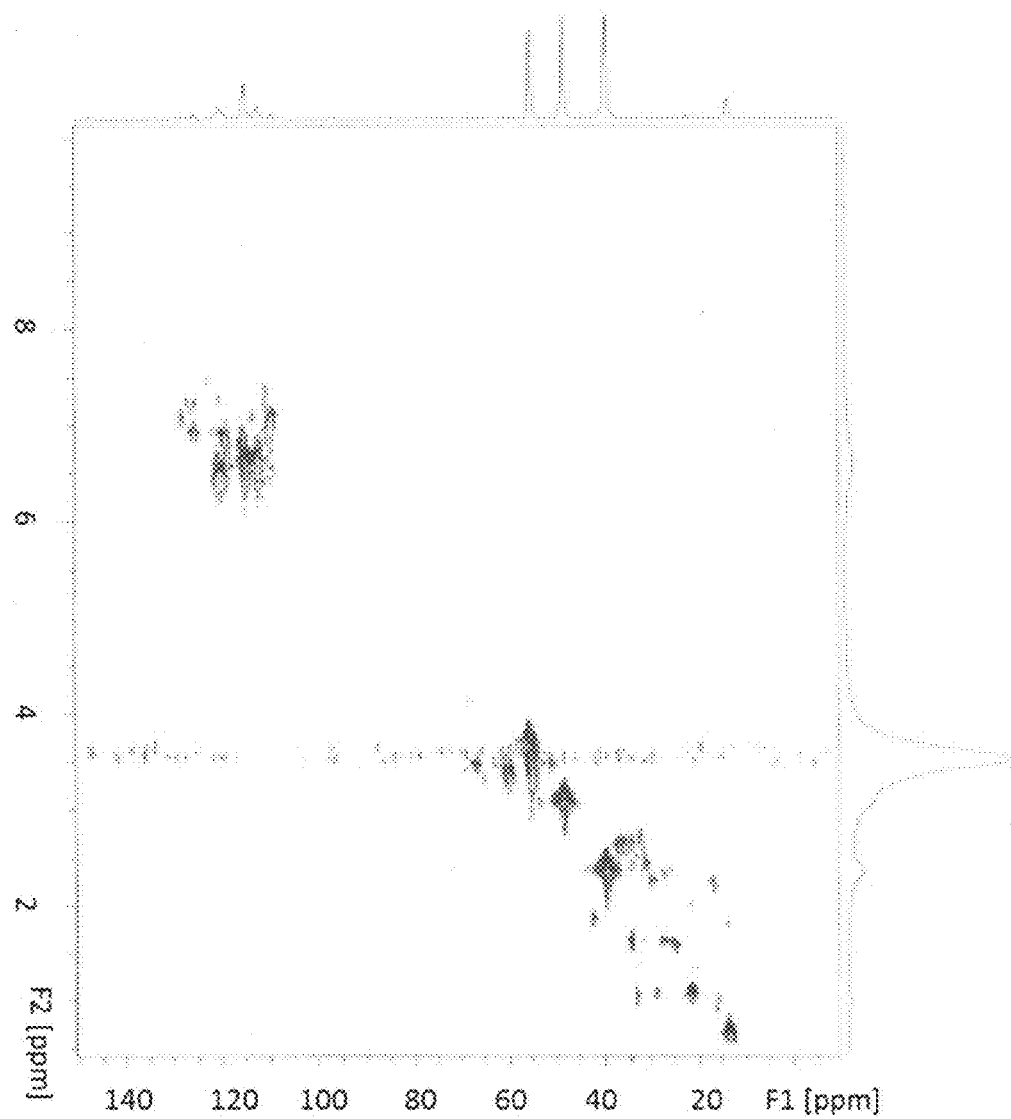
FIG. 9, HSQC of product from Example 38
Figure 10:
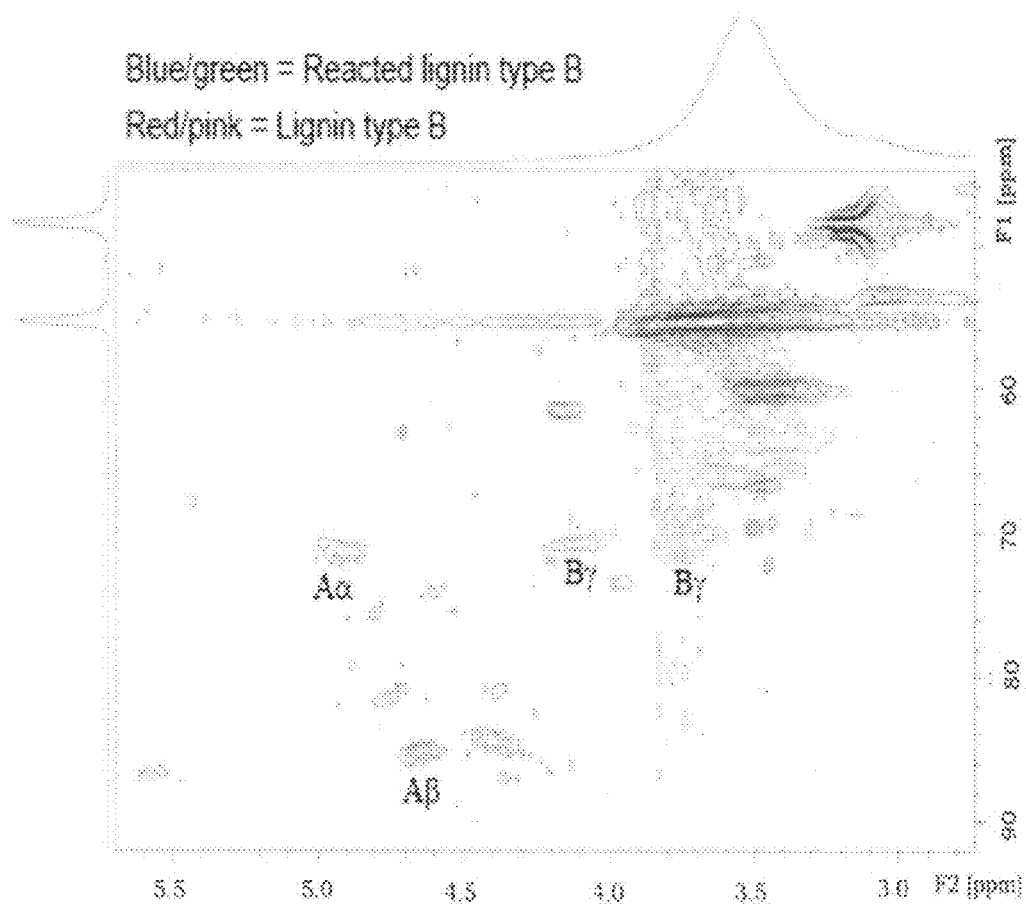
FIG. 10, HSQC Overlay: Lignin type B in red/pink, reacted lignin type B in blue/green.
Figure 10:
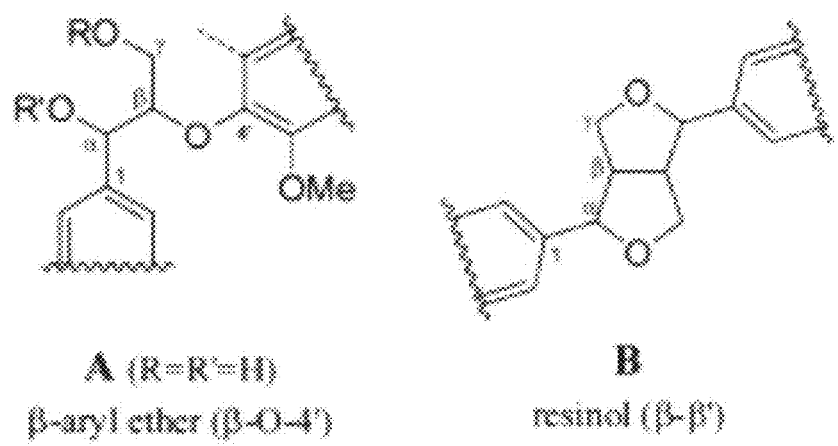
Figure 10:
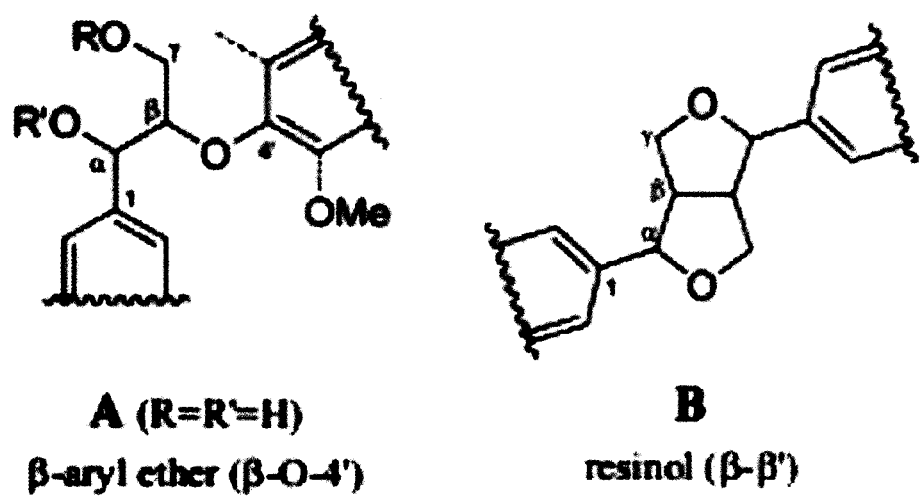
Figure 11:
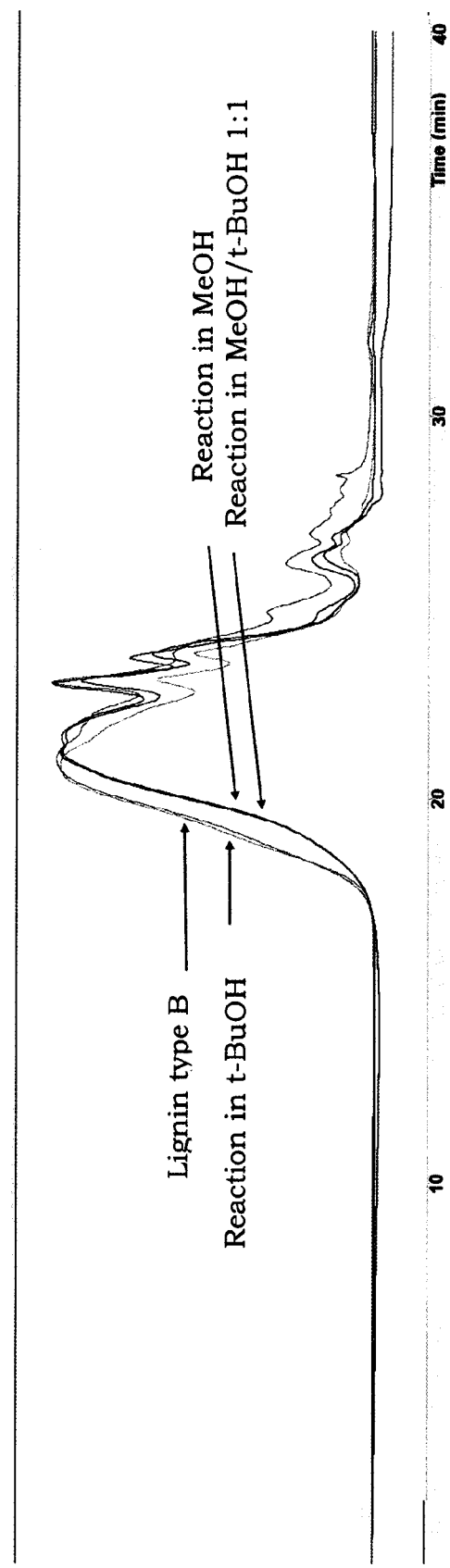
FIG. 11, shows the results from the reaction mixtures (Lignin type B and Lignin type B reacted in MeOH, in t-BuOH and in MeOH/t-BuOH FIG. 12, shows the results from the reaction mixtures Lignin type B reacted with MeOH/i-PrOH 16:1

See FIGS. 8 to 10 (HSQC) and FIG. 11 show the results from the reaction mixtures (Lignin type B reacted in MeOH, in t-BuOH and in MeOH/t-BuOH 1:1.

Example 41

Reaction of Lignin Type B, i-PrOH

Wet Raney Ni 4200 (~70 mg, $1\times10^{-3}$ mol, 500 mol %), Lignin type B (40 mg, $2.2\times10^{-4}$ mol, dry), is weighed into a reaction flask under argon. Degassed MeOH (3 mL) followed by i-PrOH (0.2 mL) is added and the flask is capped with a rubber septa and the mixture is heated (120° C.). The reaction is run for 18 hours and the reaction mixture is cooled. Nickel was removed with a magnet, and the mixture is neutralized. The reaction mixture is injected into an HPLC-system (GPC).

Figure 12:
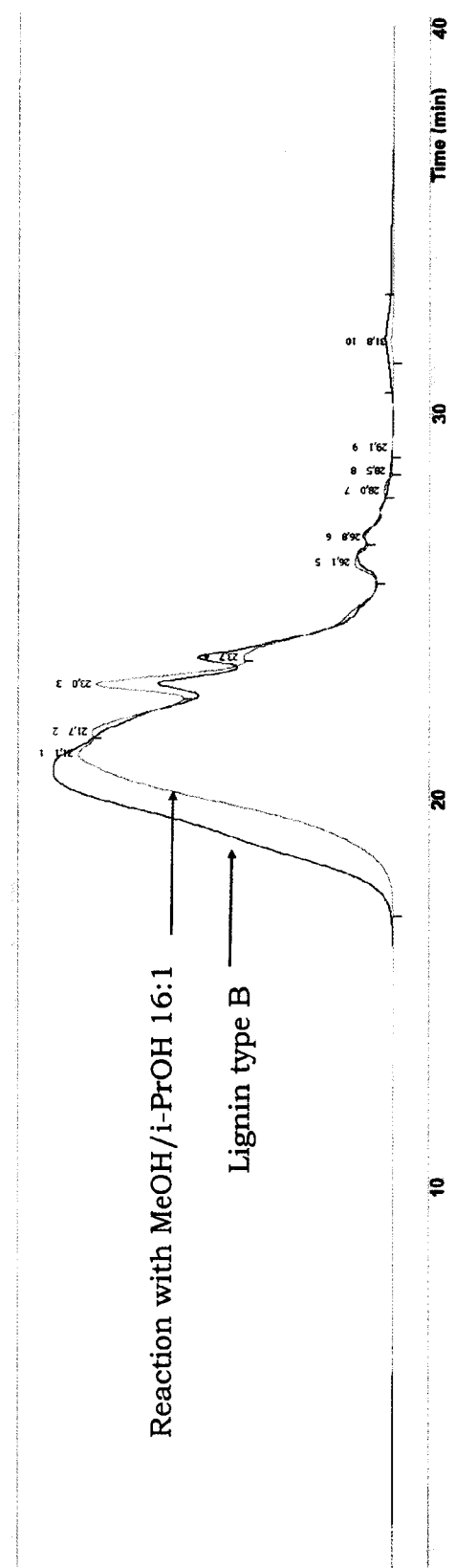

See FIG. 12, show the results from the reaction mixtures Lignin type B reacted with MeOH/i-PrOH 16:1.

Example 42

Reaction of Lignin Type B, in MeOH

Wet Raney Ni 4200 (~70 mg, $1\times10^{-3}$ mol, 500 mol %), KOH (37 mg, $6.7\times10^{-4}$ mol, 300%) Lignin type B (40 mg, $2.2\times10^{-4}$ mol, dry), is weighed into a reaction flask under argon. Degassed MeOH (3 mL) is added and the flask is capped with a rubber septa and the mixture is heated (120° C.). The reaction is run for 50 hours and the reaction mixture is cooled. Nickel was removed with a magnet, and the mixture is neutralized. The reaction mixture is injected into an HPLC-system (GPC).

Example 43

Reaction of Lignin Type B, in Glycerol

Wet Raney Ni 4200 (~70 mg, $1\times10^{-3}$ mol, 500 mol %), KOH (37 mg, $6.7\times10^{-4}$ mol, 300%) Lignin type B (40 mg, $2.2\times10^{-4}$ mol, dry), is weighed into a reaction flask under argon. Degassed Glycerol (3 mL) is added and the flask is capped with a rubber septa and the mixture is heated (150° C.). The reaction is run for 50 hours and the reaction mixture is cooled. MeOH is added and Nickel was removed with a magnet, and the mixture is neutralized. The reaction mixture is injected into an HPLC-system (GPC).

Figure 13:
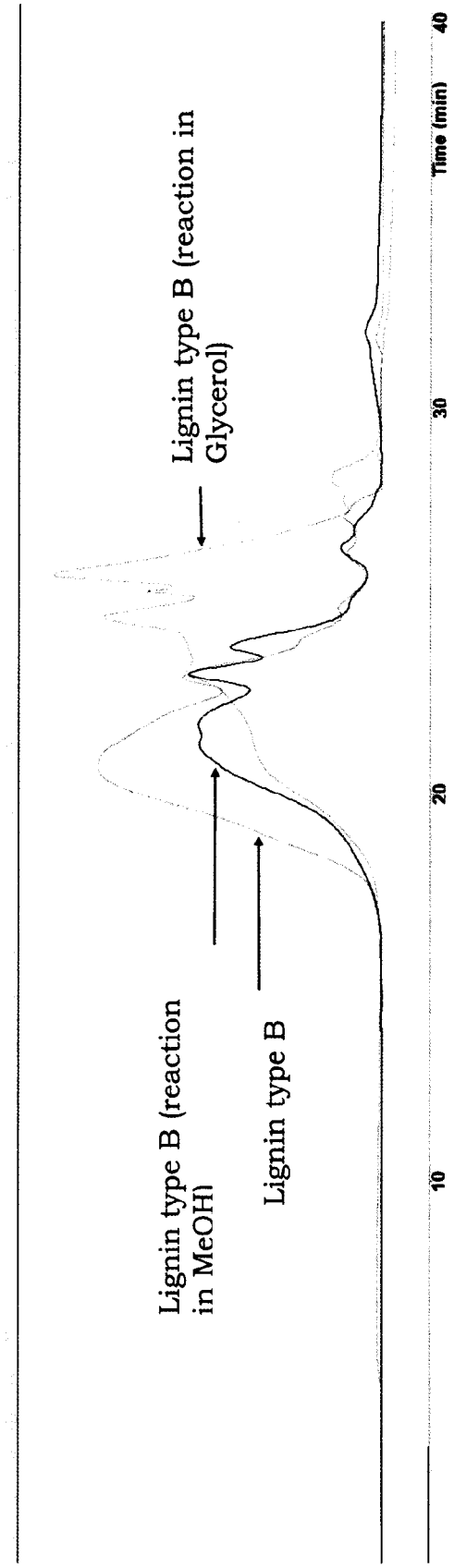
FIG. 13, shows the results from the reaction mixtures (Lignin type B reaction in glycerol and reaction in MeOH.

See FIG. 13, show the results from the reaction mixtures (Lignin type B reaction in Glycerol and reaction in MeOH.

Example 44

Reaction of Artificial Polymer

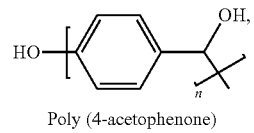

Poly (4-acetophenone)

(10 mg, $7\times10^{-5}$ mol) and wet Raney Ni 4200 (22 mg, $3.6\times10^{-4}$ mol, 500 mol %) and KOH (12 mg, $2.2\times10^{-4}$ mol, 300%) is weighed into a reaction flask under argon. Degassed MeOH (1 mL) is added and the flask is capped with a rubber septa and the mixture is heated (120° C.). The reaction is run for 24 hours and the reaction mixture is cooled. Nickel was removed with a magnet, and the mixture is neutralized. The reaction mixture is injected into an HPLC-system (GPC).

Figure 14:
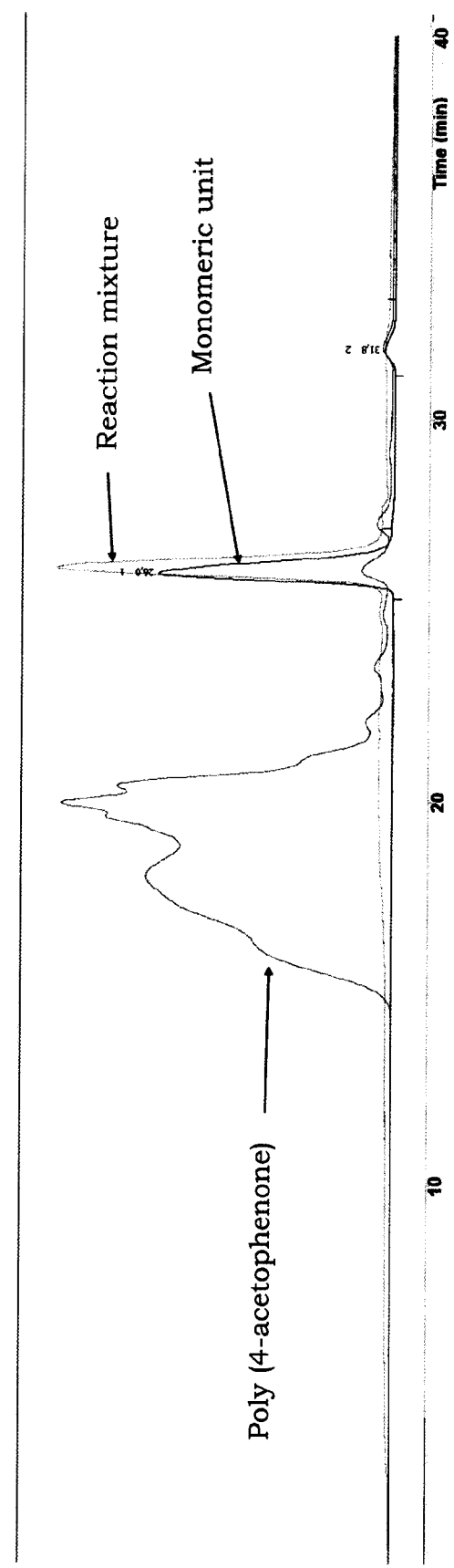
FIG. 14, GPC showing the results from the reaction mixture

See FIG. 14, show the results from the reaction mixture.

Example 45

Reaction of Artificial Polymer

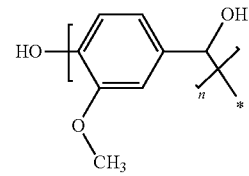

Poly (Apocynin)

(12 mg, $7\times10^{-5}$ mol) and wet Raney Ni 4200 (22 mg, $3.6\times10^{-4}$ mol, 500 mol %) and KOH (12 mg, $2.2\times10^{-4}$ mol, 300%) is weighed into a reaction flask under argon. Degassed MeOH (1 mL) is added and the flask is capped with a rubber septa and the mixture is heated (120° C.). The reaction is run for 24 hours and the reaction mixture is cooled. Nickel was removed with a magnet, and the mixture is neutralized. The reaction mixture is injected into an HPLC-system (GPC).

Figure 15:
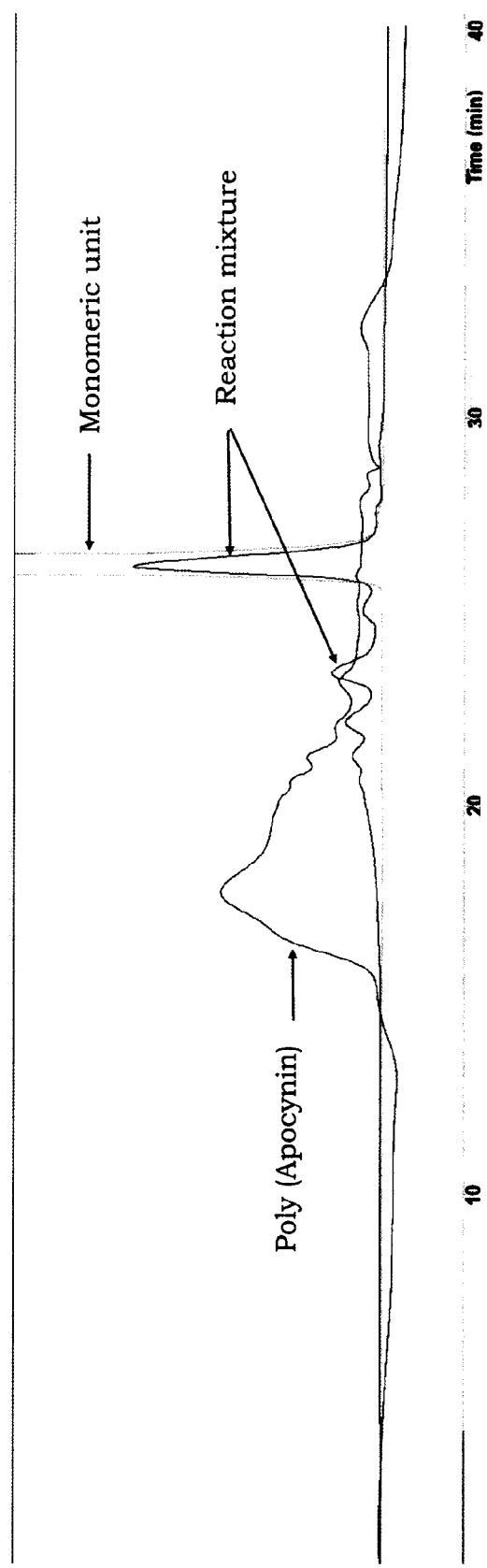
FIG. 15, GPC showing the results from the reaction mixtures.

See FIG. 15, show the results from the reaction mixtures.

Example 46

Reaction of Lignin Type B

As in Example 38 with Water Wash

Wet Raney Ni 4200 (~70 mg, $1\times10^{-3}$ mol, 500 mol %), KOH (37 mg, $6.7\times10^{-4}$ mol, 300%) and Lignin type B (40 mg, $2.2\times10^{-4}$ mol, dry), is weighed into a reaction flask under argon. Degassed methanol (3 mL) is added and the flask is capped with a rubber septa and the mixture is heated (120° C.). The reaction is run for 18 hours and the reaction mixture is cooled. Nickel was removed with a magnet, and the mixture is neutralized 3 drops of using concentrated HCl. The solvent is evaporated. 15 mL of water is added, the suspension is sonicated and the solid is filtered off. The solid reaction mixture is again dissolved in MeOH and injected into an HPLC-system (GPC). Analysis gave that water treatment did not change the size of the reacted polymer and that salts can easily be removed.

Figure 16:
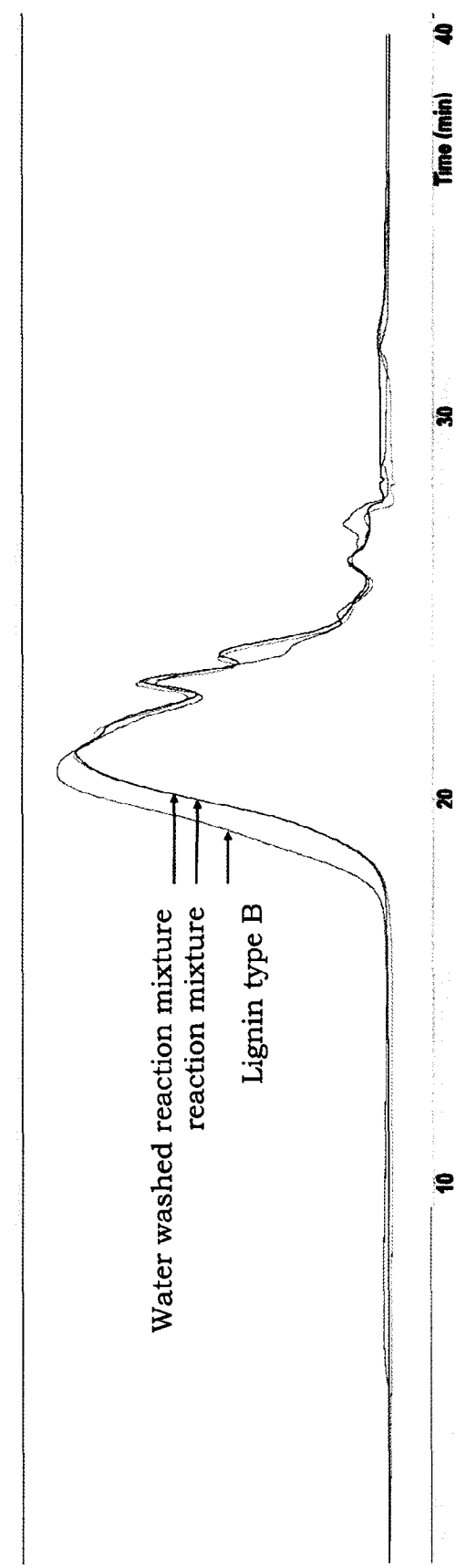
FIG. 16, showing the results from the reaction mixture and the reaction mixture after water treatment.

See FIG. 16, show the results from the reaction mixture and the reaction mixture after water treatment.

Example 47

Reaction of Lignin Type B

180° C. in Glycerol

Wet Raney Ni 4200 (~70 mg, $1\times10^{-3}$ mol, 500 mol %), KOH (37 mg, $6.7\times10^{-4}$ mol, 300%) and Lignin type B (40 mg, $2.2\times10^{-4}$ mol, dry), is weighed into a reaction flask under argon. Degassed Glycerol (3 mL) is added and the flask is capped with a rubber septa and the mixture is heated (180° C.). The reaction is run for 18 hours and the reaction mixture is cooled. Nickel was removed with a magnet, and the mixture is neutralized 3 drops of using concentrated HCl and injected into an HPLC-system (GPC). 15 mL of water is added, the suspension is sonicated and the solid is filtered off. The solid reaction mixture is again dissolved in MeOH and injected into an HPLC-system (GPC).

Figure 17:
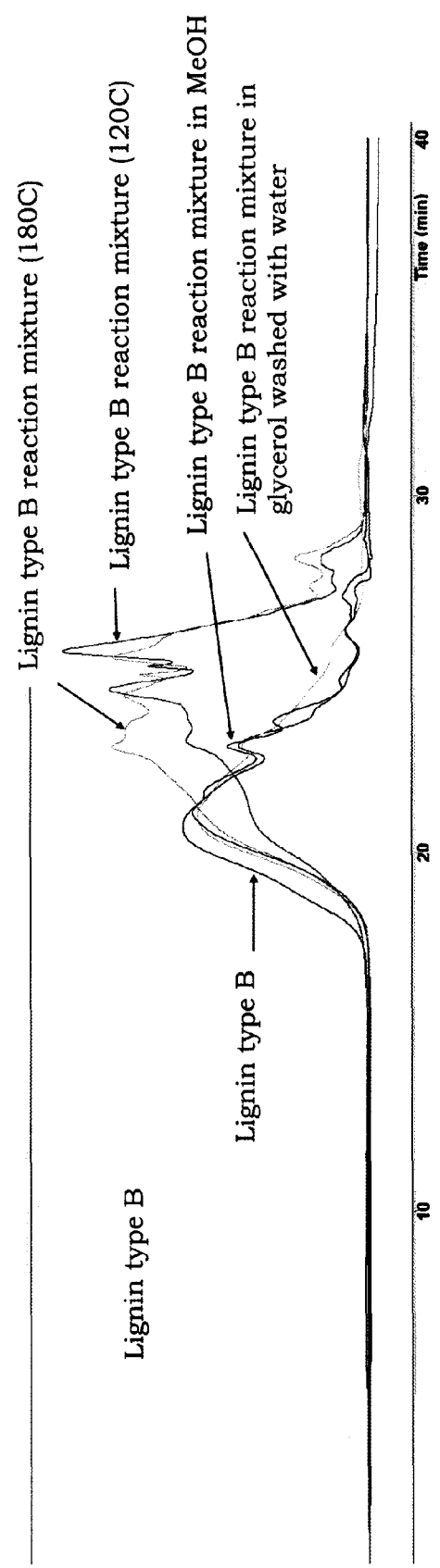
FIG. 17, show the results from the reaction mixture, water treated reaction and as a comparison reaction in MeOH

See FIG. 17, show the results from the reaction mixture, water treated reaction and as a comparison reaction in MeOH.

Example 48

Reaction of Lignin Type C

Wet Raney Ni 4200 (~30 mg, $5\times10^{-4}$ mol, 500 mol %), KOH (18 mg, $3\times10^{-4}$ mol, 300%) and Lignin type C (20 mg, dry), is weighed into a reaction flask under argon. Degassed methanol (1.5 mL) is added and the flask is capped with a rubber septa and the mixture is heated (120° C.). The reaction is run for 18 hours and the reaction mixture is cooled. Nickel was removed with a magnet, and the mixture is neutralized. The reaction mixture is injected into an HPLC-system (GPC).

Example 49

Reaction of Lignin Type C

Wet Raney Ni 4200 (~30 mg, $5\times10^{-4}$ mol, 500 mol %) and Lignin type C (20 mg, dry), is weighed into a reaction flask under argon. Degassed i-PrOH (1.5 mL) is added and the flask is capped with a rubber septa and the mixture is heated (120° C.). The reaction is run for 18 hours and the reaction mixture is cooled. Nickel was removed with a magnet, and the mixture is neutralized. The reaction mixture is injected into an HPLC-system (GPC).

Figure 18:
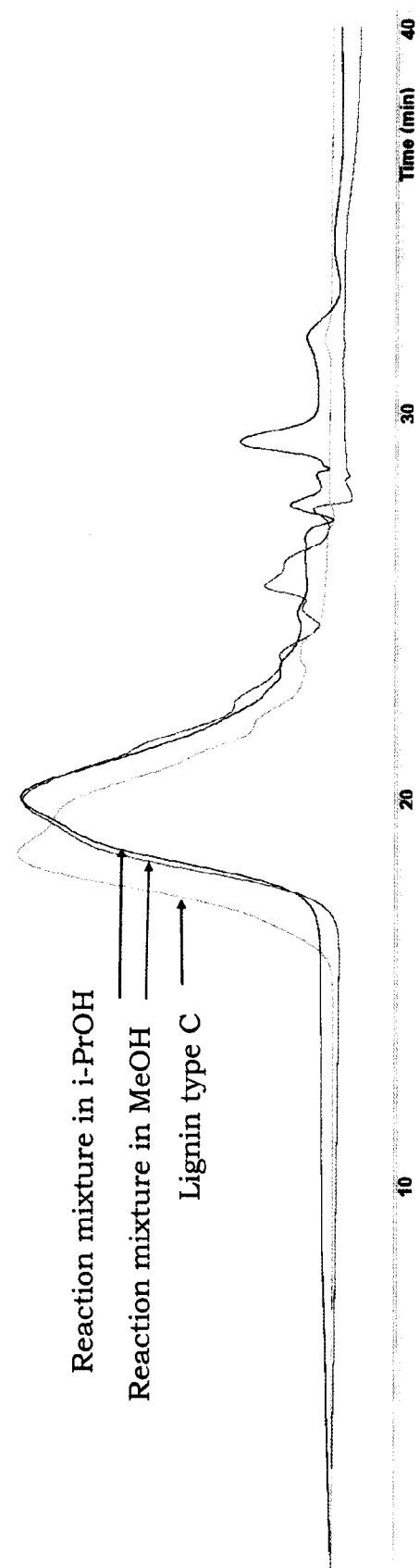
FIG. 18, shows the results from the reaction mixtures.

See FIG. 18, show the results from the reaction mixtures.

Example 50

Reaction of Lignin Type B

In Dioxane/i-PrOH 3:1

Wet Raney Ni 4200 (~70 mg, $1\times10^{-3}$ mol, 500 mol %), KOH (37 mg, $7\times10^{-4}$ mol, 300%) and Lignin type B (40 mg, $2.2\times10^{-4}$ mol, dry), is weighed into a reaction flask under argon. Degassed Dioxane (3 mL) and i-PrOH (1 mL) is added and the flask is capped with a rubber septa and the mixture is heated (120° C.). The reaction is run for 18 hours and the reaction mixture is cooled. MeOH is added and Nickel was removed with a magnet, and the mixture is neutralized. The reaction mixture is injected into an HPLC-system (GPC).

Example 51

Reaction of Lignin Type B

In Ethylene Glycol

Wet Raney Ni 4200 (~70 mg, $1\times10^{-3}$ mol, 500 mol %), KOH (37 mg, $7\times10^{-4}$ mol, 300%) and Lignin type B (40 mg, $2.2\times10^{-4}$ mol, dry), is weighed into a reaction flask under argon. Degassed ethylene glycol (3 mL) is added and the flask is capped with a rubber septa and the mixture is heated (120° C.). The reaction is run for 18 hours and the reaction mixture is cooled. MeOH is added and Nickel was removed with a magnet, and the mixture is neutralized. The reaction mixture is injected into an HPLC-system (GPC).

Figure 19:
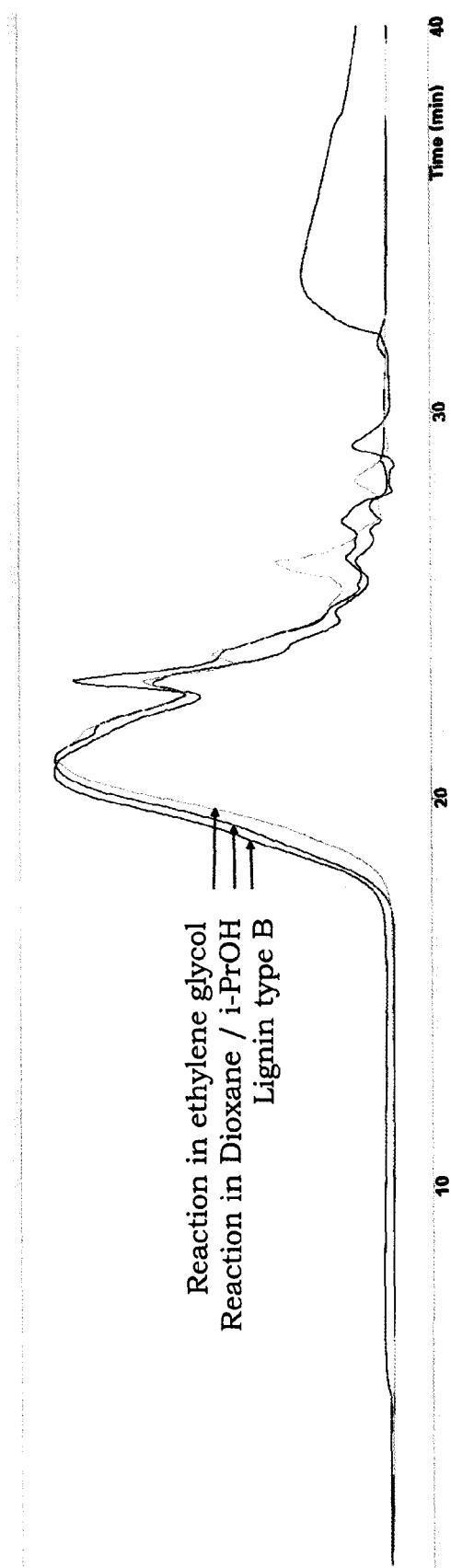
FIG. 19 shows the results from the reaction mixtures.

See FIG. 19, show the results from the reaction mixtures.

Example 52

Reaction of Lignin Type B

| Ni/KOH/MeOH | Ni/MeOH | MeOH | KOH/MeOH | Ni/Et$_3$N/MeOH |
|---|---|---|---|---|
| Rank 1 | Rank 2 | Rank 5 | Rank 3 | Rank 4 |

Omitting reagents as in table above. Procedure as follows: Lignin type B (40 mg, $2.2\times10^{-4}$ mol, dry), wet Raney Ni 4200 (~70 mg, $1\times10^{-3}$ mol, 500 mol %), KOH (37 mg, $7\times10^{-4}$ mol, 300%) or alternatively Et$_3$N (94 μL, $7\times10^{-4}$ mol, 300%) is weighed into a reaction flask under argon. Degassed MeOH (3 mL) is added and the flask is capped with a rubber septa and the mixture is heated (120° C.). The reaction is run for 18 hours and the reaction mixture is cooled. MeOH is added and Nickel was removed with a magnet, and the mixture is neutralized. The reaction mixture is injected into an HPLC-system (GPC).

Figure 20:
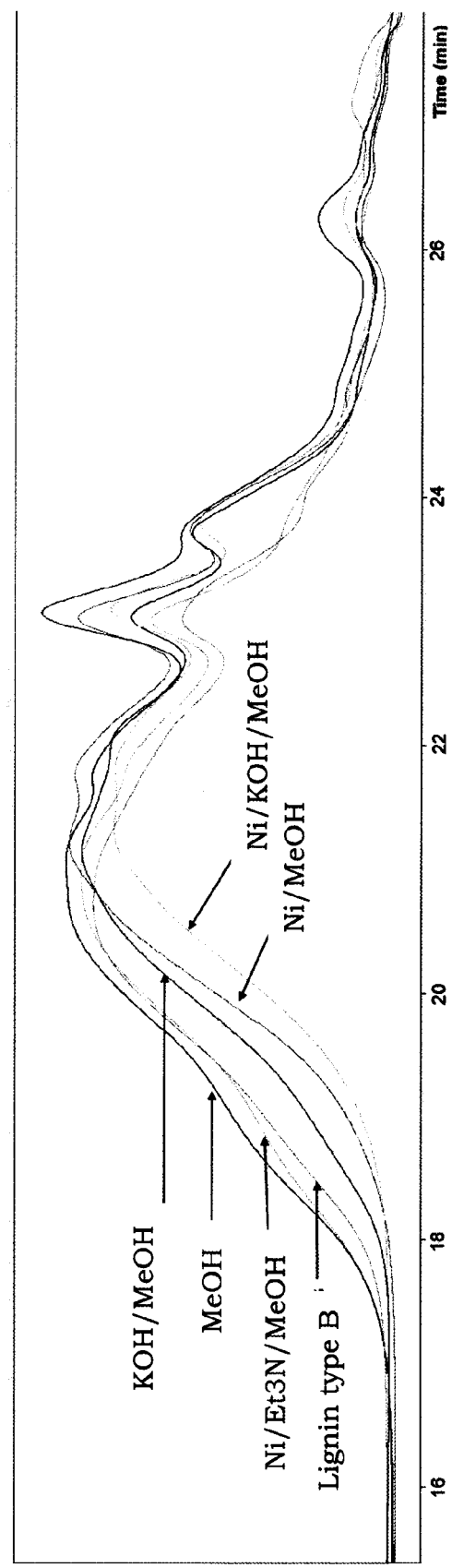
FIG. 20 shows the results from the reaction mixtures.

See FIG. 20, show the results from the reaction mixtures.

Example 53

Reaction of Lignin Type A

| Ni/KOH/MeOH | Ni/MeOH | MeOH | KOH/MeOH | Ni/Et$_3$N/MeOH |
|---|---|---|---|---|
| Rank 1 | Rank 2 | Rank 2 | Rank 2 | Rank 2 |

Omitting reagents as in table above. Procedure as follows: Lignin type A (40 mg, $2.2\times10^{-4}$ mol, dry), wet Raney Ni 4200 (~70 mg, $1\times10^{-3}$ mol, 500 mol %), KOH (37 mg, $7\times10^{-4}$ mol, 300%) or alternatively Et$_3$N (94 μL, $7\times10^{-4}$ mol, 300%) is weighed into a reaction flask under argon. Degassed MeOH (3 mL) is added and the flask is capped with a rubber septa and the mixture is heated (120° C.). The reaction is run for 18 hours and the reaction mixture is cooled. MeOH is added and Nickel was removed with a magnet, and the mixture is neutralized. The reaction mixture is injected into an HPLC-system (GPC).

Figure 21:
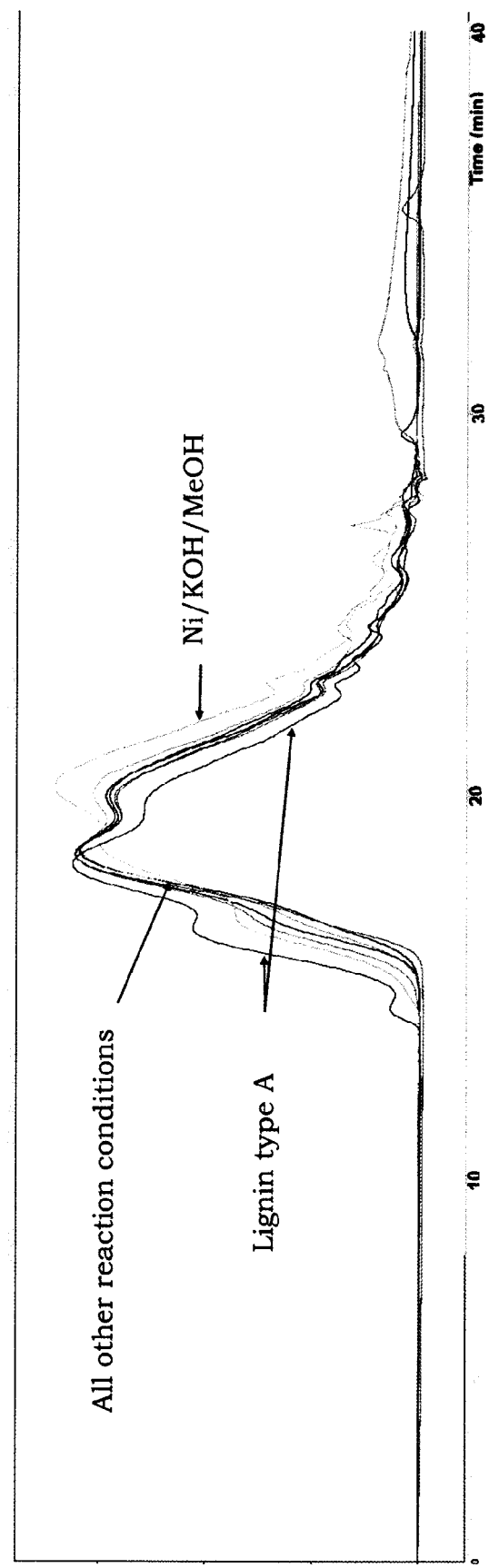
FIG. 21 shows the results from the reaction mixtures.

See FIG. 21, show the results from the reaction mixtures.

Example 54

Reaction of Lignin Type B

Lignin type B (40 mg, $2.2 \times 10^{-4}$ mol, dry), wet Raney Ni 4200 (~70 mg, $1 \times 10^{-3}$ mol, 500 mol %), base ($7 \times 10^{-4}$ mol, 300%) [Bases used: NaOH (27 mg), $K_2CO_3$ (92 mg), $NaBH_4$ (25 mg), $NH_4COOH$ (42 mg)] is weighed into a reaction flask under argon. Degassed MeOH (3 mL) is added and the flask is capped with a rubber septa and the mixture is heated (120° C.). The reaction is run for 18 hours and the reaction mixture is cooled. MeOH is added and Nickel was removed with a magnet, and the mixture is neutralized. The reaction mixture is injected into an HPLC-system (GPC).

Figure 22:
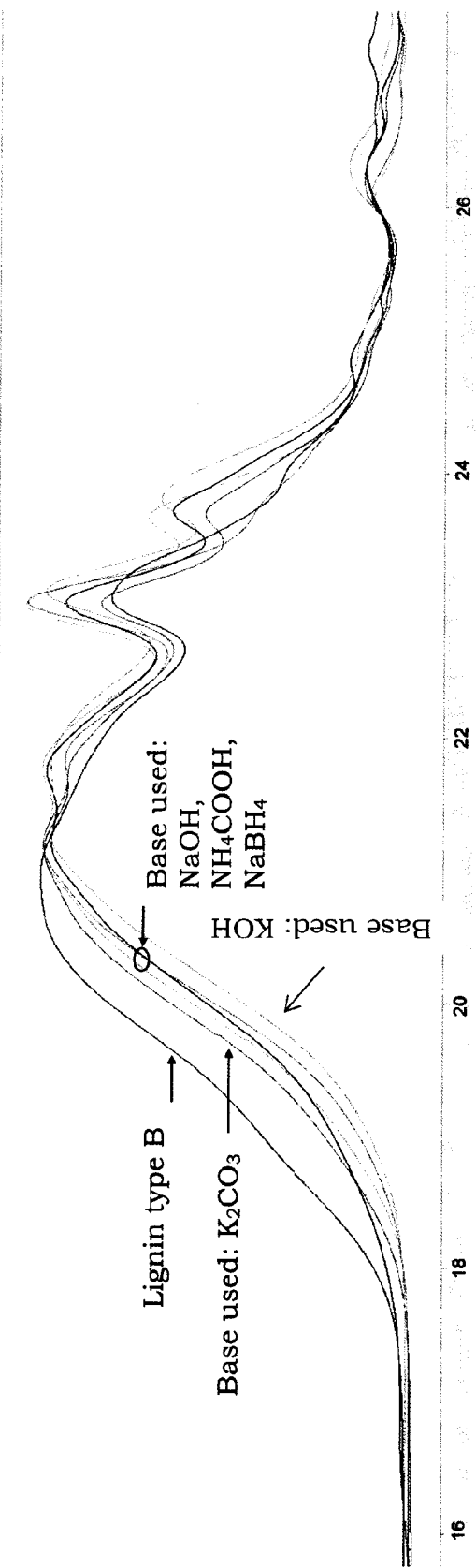
FIG. 22 shows the results from the reaction mixtures.

See FIG. 22, show the results from the reaction mixtures.

Example 55

Reaction of Lignin Type D

Lignin type D (80 mg, $4.4 \times 10^{-4}$ mol, dry), wet Raney Ni 4200 (~140 mg, $2 \times 10^{-3}$ mol, 500 mol %), KOH (74 mg, $1.4 \times 10^{-3}$ mol, 300%) is weighed into a reaction flask under argon. Degassed MeOH (6 mL) and water (2 mL) is added and the flask is capped with a rubber septa and the mixture is heated (120° C.). The reaction is run for 18 hours and the reaction mixture is cooled. Nickel was removed with magnet, and the reaction was neutralized with 2 drops of concentrated HCl. The mixture was concentrated, washed with 10 mL of water and dried. 30 mg of a solid was collected. The solid was dissolved in THF/MeOH 1:1 and the mixture was injected into an HPLC-system (GPC). The starting material is not soluble in THF but soluble in water and cannot be analyzed in the GCP. After the reaction a THF soluble solid was collected in 38% yield.

Figure 23:
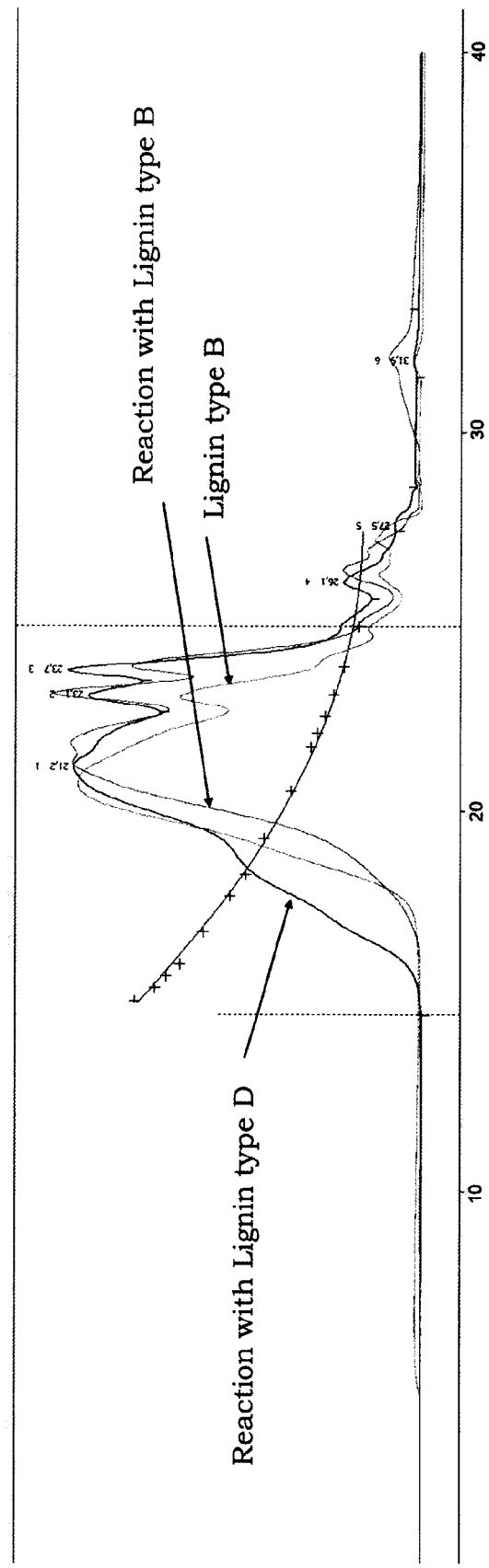
FIG. 23 shows the results from the reaction mixtures.

See FIG. 23, show the results from the reaction mixtures.

Figure 24:
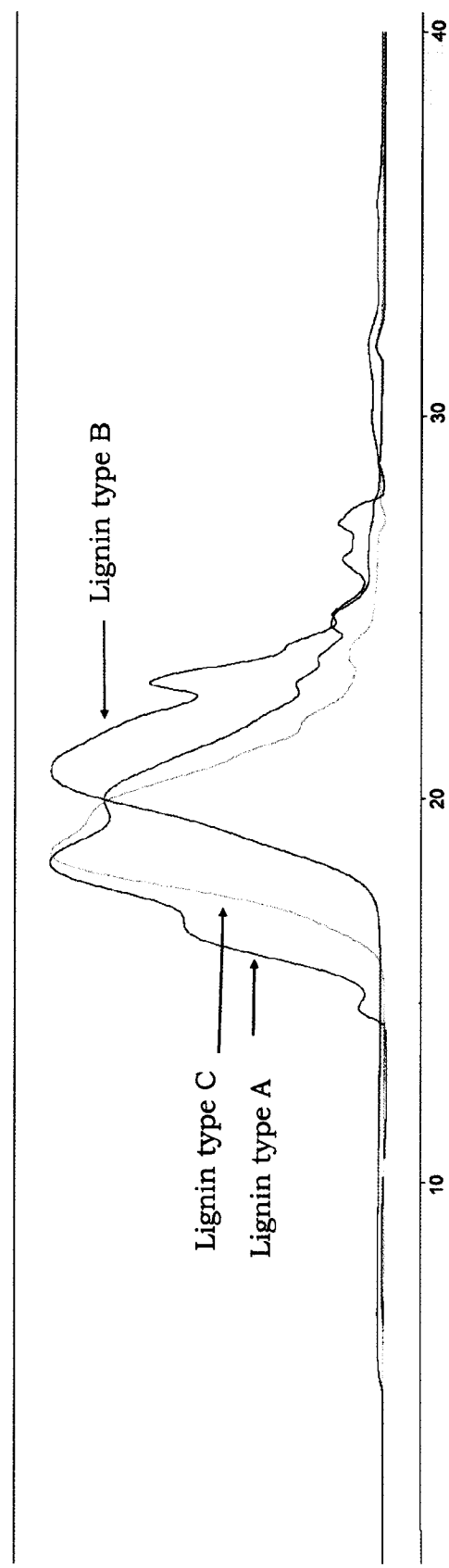
FIG. 24 compares different lignin sources, Lignin type A, B and C.

See FIG. 24, compares different lignin sources. Lignin type A, Lignin type B. Lignin type C.

Example 57

2-phenoxy-1-phenylethanol

Nickel on carbon (50 mg, $20 \times 10^{-4}$ mol, 10 mol %) is weighed into a reaction flask. Isopropanol (4 mL) and 2-phenoxy-1-phenylethanol ($1.6 \times 10^{-4}$ mol, 34 mg), is added and the flask capped with a rubber septa and the mixture is heated (80° C.). The reaction is run for 4 hours and the reaction mixture is filtered. The solvents are evaporated and the product is purified by column chromatography. The product acetophenone and phenol was analyzed by $^1H$ NMR and produced in 80% yield.

Example 58

Reaction of Lignin Type B in Glycerol at 180° C. for 60 min

Wet Raney Ni 4200 (~70 mg, $1 \times 10^{-3}$ mol, 500 mol %), KOH (37 mg, $6.7 \times 10^{-4}$ mol, 300%) and Lignin type B (40 mg, $2.2 \times 10^{-4}$ mol, dry), is weighed into a reaction flask under argon. Degassed methanol (3 mL) is added and the flask is capped with a rubber septa and the mixture is heated (180° C.). The reaction is run for 60 minutes and the reaction mixture is cooled. The reaction is diluted with MeOH/THF, the mixture was neutralized and nickel was removed with a magnet. The reaction mixture is injected into an HPLC-system (GPC). The results showed that the reaction was fully completed.

Example 59

Reaction of Lignin Type B at 45° C.

Wet Raney Ni 4200 (~70 mg, $1 \times 10^{-3}$ mol, 500 mol %), KOH (37 mg, $6.7 \times 10^{-4}$ mol, 300%) and Lignin type B (40 mg, $2.2 \times 10^{-4}$ mol, dry), is weighed into a reaction flask under argon. Degassed methanol (3 mL) is added and the flask is capped with a rubber septa and the mixture is heated (45° C.). The reaction is run for 50 hours and the reaction mixture is cooled. Nickel was removed with a magnet, and the mixture is neutralized. The reaction mixture is injected into an HPLC-system (GPC). The results showed that the reaction had gone half way.

Example 60

Reaction of Lignin Type C with Pd/C

Pd/C (5 wt %) (0.027 g, 5 mol %), $NH_4HCO_2$ (0.064 g, 1.0 mmol) and lignin type C (0.050 g, 0.252 mmol) were added to a 5 mL vial. The vial was sealed and 2.4 mL of ethyl acetate and 0.6 mL of water were added via syringe. Another needle was inserted through a septum to release pressure during the solvent addition. The needle was removed and the vial was placed in a preheated oil bath (120° C.) with a stirring speed of 1000 rpm for 24 h. The vial was cooled to room temperature and then formic acid (20 μL, 0.5 mmol) was added via syringe and the reaction was run for 12 h. The vial was cooled to room temperature and reaction mixture was filtrated through a filter paper, using acetone (10 mL) following by ethanol (10 mL) as eluent. Solvent was removed in vaccuo and the crude oil was co-evaporated two times with 15 mL of ethanol (99.5%). The oil obtained was analyzed by 2D NMR (HSQC). The reaction mixture is injected into an HPLC-system (GPC).

Example 61

Reaction of Lignin Type B at 120° C. for 60 min

Wet Raney Ni 4200 (~70 mg, $1 \times 10^{-3}$ mol, 500 mol %), KOH (37 mg, $6.7 \times 10^{-4}$ mol, 300%) and Lignin type B (40 mg, $2.2 \times 10^{-4}$ mol, dry), is weighed into a reaction flask under argon. Degassed methanol (3 mL) is added and the flask is capped with a rubber septa and the mixture is heated (45° C.). The reaction is run for 50 hours and the reaction mixture is cooled. Nickel was removed with a magnet, and the mixture is neutralized. The reaction mixture is injected into an HPLC-system (GPC).

Example 62

Reaction of Lignin Type E

Lignin type E (40 mg, $2.2 \times 10^{-4}$ mol, dry), wet Raney Ni 4200 (~70 mg, $1 \times 10^{-3}$ mol, 500 mol %), KOH (37 mg, $0.7 \times 10^{-3}$ mol, 300%) is weighed into a reaction flask under argon. Degassed MeOH (3 mL) is added and the flask is capped with a rubber septa and the mixture is heated (120° C.). The reaction is run for 18 hours and the reaction mixture is cooled. Nickel was removed with magnet, and the reaction was neutralized with 2 drops of concentrated HCl. The product was mostly not dissolved in THF/MeOH 1:1 but the soluble mixture was injected into an HPLC-system (GPC). The starting material is not soluble in THF but soluble in water and cannot be analyzed in the GCP. After the reaction a THF soluble solid was collected in 5% yield.

Example 63

Reaction of Lignin Type C with Pd/C

Pd/C (5 wt %) (0.054 g, 0.02 mmol, 10 mol %), KOH (0.037 g, 0.67 mmol, 300 mol %) and lignin type B (0.040 g, 0.22 mmol) were added to a 5 mL vial. The vial was sealed and 3 mL of MeOH were added. The vial was placed in a preheated oil bath (120° C.) and the reaction was run for 12 h. The vial was cooled to room temperature and reaction mixture was filtrated through a filter paper, using THF/MeOH. The reaction mixture is injected into an HPLC-system (GPC).

Example 64

Reaction of Lignin Type C in Acetone

Wet Raney Ni 4200 (~30 mg, $5\times10^{-4}$ mol, 500 mol %) and Lignin type C (20 mg, dry), is weighed into a reaction flask under argon. Degassed acetone (5 mL) is added and the flask is capped with a rubber septa and the mixture is heated (120° C.). The reaction is run for 18 hours and the reaction mixture is cooled. Nickel was removed with a magnet, and the mixture is neutralized. The reaction mixture is injected into an HPLC-system (GPC).

Example 64

Reaction of Lignin Type C, Water Wash and a Second Reduction Step

Wet Raney Ni 4200 (~70 mg, $1\times10^{-3}$ mol, 500 mol %), KOH (37 mg, $6.7\times10^{-4}$ mol, 300%) and Lignin type C (40 mg, $2.2\times10^{-4}$ mol, dry), was weighed into a reaction flask under argon. Degassed methanol (3 mL) is added and the flask was capped with a rubber septa and the mixture is heated (120° C.). The reaction was run for 18 hours and the reaction mixture was cooled. Nickel was removed with a magnet, and the mixture was neutralized using 3 drops of concentrated HCl. The solvent was evaporated. 15 mL of water was added, the suspension was sonicated and the solid was filtered off. The solid reaction mixture was again dissolved in MeOH and injected into a HPLC-system (GPC).

Figure 25:
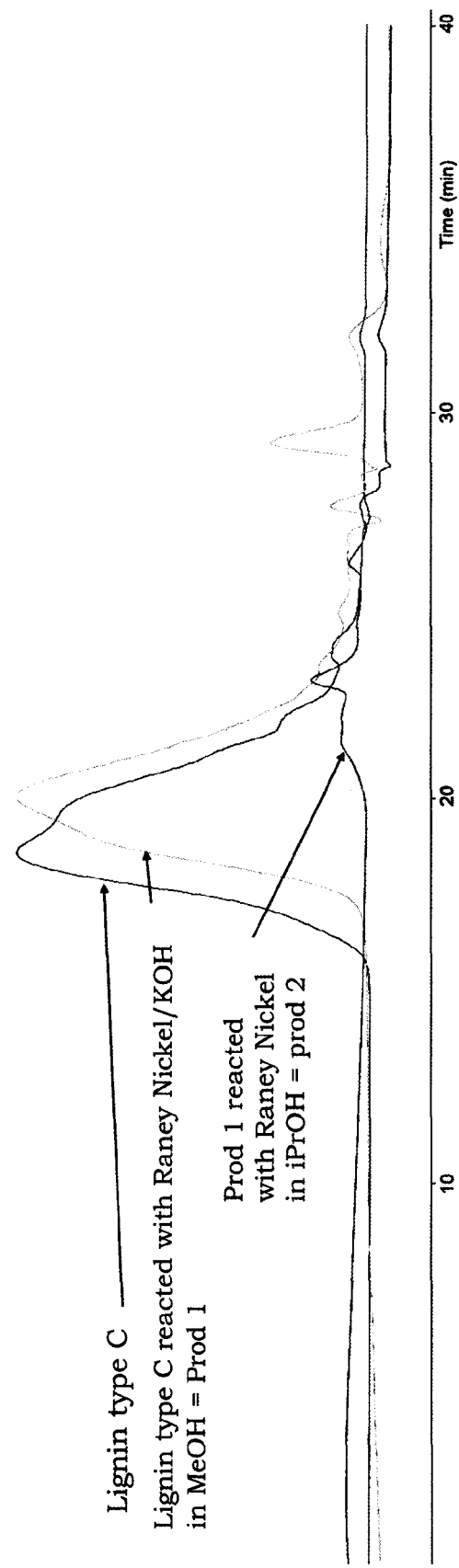
FIG. 25 shows the results from the reaction mixture and the reaction mixture after water treatment.

See FIG. 25, show the results from the reaction mixture after water treatment.

Figure 26:
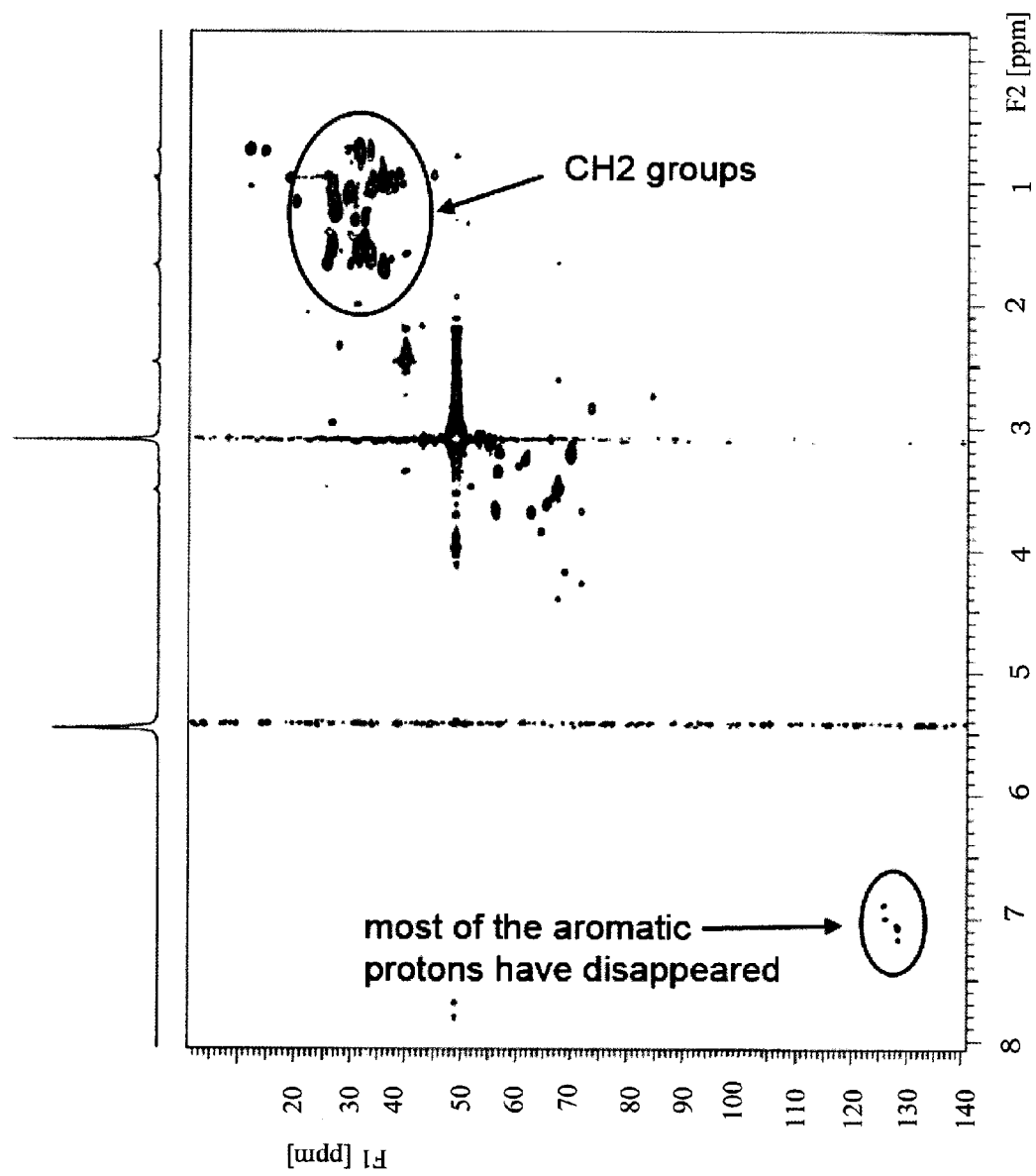
FIG. 26 shows HSQC experiment from Prod 2.

The product (Prod 1) obtained above was dissolved in 3 mL degassed isopropanol and again Wet Raney Ni 4200 (~70 mg, $1\times10^{-3}$ mol, 500 mol %) was added. The flask was capped with a rubber septa and the mixture is heated (120° C.). The reaction is run for 18 hours and the reaction mixture was cooled. Nickel was removed with a magnet. The solvent was evaporated, giving a second product mixture (Prod 2). The reaction mixture was again dissolved in THF and injected into an HPLC-system (GPC). Analysis gave a very weak signal. NMR (HSQC) analysis showed that most of the aromatic protons had disappeared and new CH2 signals had appeared, FIG. 26. Benzene rings present in lignin type C is reduced to cyclohexanes.

The invention claimed is:

1. A method of cleaving a β-O-4 bond in a substrate, the method comprising:
   providing a substrate, a hydrogen donor, a transition metal based catalyst and at least one solvent, wherein the hydrogen donor is at least one of an alcohol and a formic acid;
   forming a mixture of the substrate, the hydrogen donor, the transition metal based catalyst and the solvent; and
   letting the mixture react in order to cleave the β-O-4 bond in the substrate at a temperature of not higher than 200° C.,
   wherein the substrate is a lignin.

2. The method according to claim 1, wherein the hydrogen donor is one of glycol, glucose, glycerol, ethanol, methanol, butanol or isopropanol and mixtures thereof.

3. The method according to claim 1, wherein the solvent is one of polar and non-polar, and wherein the solvent may be one of protic and aprotic.

4. The method according to claim 1, wherein the solvent is water when the formic acid is used as the hydrogen donor.

5. The method according to claim 1, wherein the reaction is conducted at a temperature of at least 25° C.

6. The method according claim 1, wherein the catalyst is one of a nickel based and a palladium based catalyst.

7. The method according to claim 1, wherein the amount of catalyst is a catalytic amount.

8. The method according to claim 1, wherein a base is added to the mixture.

9. The method according to claim 8, wherein said base is one of KOH, NaOH, $NaBH_4$, $NH_4COOH$ and $K_2CO_3$.

10. The method according to claim 3, wherein the solvent is an alkane.

11. The method according to claim 3, wherein the solvent is an alcohol.

12. The method according to claim 3, wherein the solvent is one of an ether and an ester.

13. The method according to claim 1, wherein more than 50% of the β-O-4 bonds are cleaved.

14. The method according to claim 1, wherein the solvent is a mixture of methanol and iso-propanol.

15. The method according to claim 1, wherein a second solvent is added during the reaction and the second solvent is iso-propanol.

16. The method of claim 5, wherein the reaction is conducted at a temperature of 70-120° C.

17. The method of claim 6, wherein the nickel based catalyst is one of Raney nickel and nickel on carbon.

18. The method according to claim 1, wherein the amount of catalyst is 1 equivalent or more.

19. The method according to claim 1, wherein the amount of catalyst is 1.5 equivalents or more.

20. The method according to claim 1, wherein the amount of catalyst is 2 equivalents or more.

21. The method according to claim 1, wherein the amount of catalyst is 3 equivalents or more.

* * * * *